(12) United States Patent
Allen et al.

(10) Patent No.: US 7,657,125 B2
(45) Date of Patent: Feb. 2, 2010

(54) TIME-LAPSING DATA METHODS AND SYSTEMS

(75) Inventors: Paul G. Allen, Seattle, WA (US);
Edward K. Y. Jung, Bellevue, WA (US);
Royce A. Levien, Lexington, MA (US);
Mark A. Malamud, Seattle, WA (US);
John D. Rinaldo, Jr., Bellevue, WA (US)

(73) Assignee: Searete LLC, Bellevue, WA (US)

( * ) Notice: Subject to any disclaimer, the term of this patent is extended or adjusted under 35 U.S.C. 154(b) by 794 days.

(21) Appl. No.: 10/972,319

(22) Filed: Oct. 22, 2004

(65) Prior Publication Data

US 2006/0088227 A1   Apr. 27, 2006

Related U.S. Application Data

(63) Continuation-in-part of application No. 10/951,002, filed on Sep. 27, 2004, now Pat. No. 7,259,731, and a continuation-in-part of application No. 10/941,803, filed on Sep. 15, 2004, and a continuation-in-part of application No. 10/912,271, filed on Aug. 5, 2004, now Pat. No. 7,133,003, and a continuation-in-part of application No. 10/910,421, filed on Aug. 2, 2004, now Pat. No. 7,283,106.

(51) Int. Cl.
G06K 9/54 (2006.01)
G06K 9/00 (2006.01)
A61B 5/05 (2006.01)

(52) U.S. Cl. .................. 382/305; 382/128; 600/410

(58) Field of Classification Search .......... 382/128–134, 382/154, 305, 312; 600/410, 439; 345/32; 705/2
See application file for complete search history.

(56) References Cited

U.S. PATENT DOCUMENTS

| | | | |
|---|---|---|---|
| 3,838,525 A | 10/1974 | Harvey | |
| 3,934,226 A | 1/1976 | Stone et al. | |
| 4,309,094 A | 1/1982 | Bollen | |
| 5,198,936 A | 3/1993 | Stringfellow | |
| 5,997,149 A | 12/1999 | Chu | |
| 6,032,119 A | 2/2000 | Brown et al. | |
| 6,071,236 A | 6/2000 | Iliff | |
| 6,077,225 A * | 6/2000 | Brock-Fisher | 600/439 |
| 6,095,985 A | 8/2000 | Raymond et al. | |
| 6,120,467 A | 9/2000 | Schallhorn | |
| 6,238,337 B1 | 5/2001 | Kambhatla et al. | |
| 6,272,468 B1 | 8/2001 | Melrose | |
| 6,322,502 B1 | 11/2001 | Schoenberg et al. | |

(Continued)

FOREIGN PATENT DOCUMENTS

JP   05181216 A2   7/1993

(Continued)

OTHER PUBLICATIONS

Radford, Tim, "Mirror, Mirror on the Wall, Who'll Be Fattest of Them All?", The Guardian Unlimited, bearing a date of Feb. 3, 2005, pp. 1-4, located at http://www.guardian.co.uk/uk_news/story/0,3604,1404636,00.html, printed on Feb. 4, 2005.

(Continued)

Primary Examiner—Kanji Patel

(57) ABSTRACT

Time-lapsing mirror methods and related systems.

46 Claims, 25 Drawing Sheets

U.S. PATENT DOCUMENTS

| | | | |
|---|---|---|---|
| 6,336,900 | B1 | 1/2002 | Alleckson et al. |
| 6,402,689 | B1 | 6/2002 | Scarantino et al. |
| 6,440,090 | B1 | 8/2002 | Schallhorn |
| 6,454,708 | B1 | 9/2002 | Ferguson et al. |
| 6,468,263 | B1 | 10/2002 | Fischell et al. |
| 6,477,394 | B2 * | 11/2002 | Rice et al. ............. 600/318 |
| 6,516,210 | B1 | 2/2003 | Foxall |
| 6,542,204 | B1 | 4/2003 | Ohzawa et al. |
| 6,556,977 | B1 | 4/2003 | Lapointe et al. |
| 6,569,094 | B2 | 5/2003 | Suzuki et al. |
| 6,574,742 | B1 | 6/2003 | Jamroga et al. |
| 6,678,703 | B2 | 1/2004 | Rothschild et al. |
| 6,710,927 | B2 | 3/2004 | Richards |
| 6,725,200 | B1 | 4/2004 | Rost |
| 6,746,122 | B2 | 6/2004 | Knox |
| 6,755,539 | B2 | 6/2004 | Brennesholtz |
| 6,757,087 | B1 | 6/2004 | Taketomi et al. |
| 6,760,515 | B1 | 7/2004 | Wang et al. |
| 6,761,458 | B2 | 7/2004 | Sakata et al. |
| 6,762,870 | B2 | 7/2004 | De Vaan |
| 6,768,915 | B2 * | 7/2004 | Brand et al. ............. 600/410 |
| 6,774,869 | B2 | 8/2004 | Biocca et al. |
| 6,869,772 | B2 * | 3/2005 | Lichtman et al. ......... 435/40.5 |
| 7,080,910 | B2 | 7/2006 | Engle |
| 7,133,003 | B2 | 11/2006 | Allen et al. |
| 7,259,731 | B2 | 8/2007 | Allen et al. |
| 7,259,732 | B2 | 8/2007 | Allen et al. |
| 7,283,106 | B2 | 10/2007 | Allen et al. |
| 2001/0031081 | A1 * | 10/2001 | Quan et al. ............. 382/154 |
| 2001/0037191 | A1 | 11/2001 | Furuta et al. |
| 2002/0196333 | A1 | 12/2002 | Gorischek |
| 2003/0041871 | A1 | 3/2003 | Endo et al. |
| 2004/0095359 | A1 | 5/2004 | Simon et al. |
| 2005/0027567 | A1 * | 2/2005 | Taha ...................... 705/2 |
| 2005/0035313 | A1 | 2/2005 | Garssen et al. |
| 2005/0174473 | A1 | 8/2005 | Morgan et al. |
| 2005/0185278 | A1 | 8/2005 | Horsten et al. |
| 2006/0017605 | A1 | 1/2006 | Lovberg et al. |

FOREIGN PATENT DOCUMENTS

| | | |
|---|---|---|
| JP | 06055957 A2 | 3/1994 |
| WO | WO 02/080773 A1 | 10/2002 |

OTHER PUBLICATIONS

Azuma, Ronald; Baillot, Yohan; Behringer, Reinhold; Feiner, Steven; Julier, Simon; MacIntyre, Blair; "Recent Advances in Augmented Reality," pp. 34-47; located at www.cs.unc.edu/~azuma/cga2001.pdf; bearing a date of Nov./Dec. 2001; printed on Jul. 12, 2004.

Butz, Andreas; Beshers, Clifford; Feiner, Steven; "Of Vampire Mirrors and Privacy Lamps: Privacy Management in Multi-User Augmented Environments," pp. 171-172; located at http://www1.cs.columbia.edu/~butz/publications/papers/uist98.pdf; bearing a date of Nov. 2-4, 1998; printed on Jul. 12, 2004.

Computer Vision & Robotics Laboratory Beckman Institute, "Multiview Mirror Pyramid Panoramic Cameras," Tan, Kar-Han; Hua, Hong; Ahuja, Narendar from the Beckman Institute for Advanced Science and Technology, University of Illinois at Urbana-Champaign, pp. 1-4 located at http://vision.ai.uiuc.edu/~tankh/Camera/camera.html printed on Aug. 9, 2004.

Francois, Alexandre R.J.; Kang, Elaine; "The Virtual Mirror," pp. 1-5; located at http://iris.usc.edu/~afrancoi/virtual mirror/; printed on Jul. 12, 2004.

Fulford, Benjamin, "Adventures in the Third Dimension" pp. 1-3 located at www.forbes.com/forbes/2004/0524/166_print.html bearing a date of May 24, 2004 and printed on Sep. 1, 2004.

Healthy Style Products, "Emjoi—The Mirror AP-13," pp. 1-2 located at http://www.healthystyleproducts.com/mirror.html printed on Sep. 1, 2004.

Highbeam Research; "Winntech. (Globalshop 2003 Spotlight);" pp. 1; located at http://www.highbeam.com/library/doc0.asp?docid=1G1:99048681&refid=ink_g5sl&skeyw; printed on Jul. 12, 2004.

Lin, I-Chen; Yeh, Jeng-Sheng; and Ouhyoung, Ming from National Taiwan University, "Extracting 3D Facial Animation Parameters from Multiview Video Clips," pp. 2-10, bearing a date of Nov./Dec. 2002 and printed on Sep. 1, 2004.

Lin, I-Chen, "The Software Tool of Mass 3D Facial Animation Parameter Extraction from Mirror-Reflected Multi-View Video User's Instruction Version 1.0," located at http://www.cmlab.csie.ntu.edu.tw/~ichen, pp. 1-24 (+ cover sheet), printed on Sep. 1, 2004.

Morimoto, Carlos Hitoshi; "Interactive Digital Mirror," from XIV Brazilian Symposium on Computer Graphics and Image Processing (SIBGRAPI'01), Oct. 15-18, 2001; pp. 1; located at http://csdl.computer.org/comp/proceeding/sibgrapi/2001/1330/00/13300232abs.htm; bearing a date of 2001; printed on Jul. 12, 2004.

Nextag, "Accessories—compare prices, review and buy at NexTag—Price—Review re Jerdon Mirror,"pp. 1-2 located at http://www.nextag.com/Jerdon_Accessories~2702144zJerdonz0zB36ozmainz5-htm printed on Sep. 1, 2004.

NP Review.Info, "New Product Reviews: New New Product Review—Jerdon JGL9W 5X Magnification Tri-fold Lighted Mirror Product Review," pp. 1-3 located at http://www.npreview.info/Home-and-Garden/Home-Decor/Mirrors/Vanity-Mirrors/Jerdon-JGL9W-5X-Magnification-Tri-fold-Lighted-Mirror.html printed on Sep. 1, 2004.

Riviere, Cameron; Taylor, Russ; Digioia, A.; Wenz, J.; Kostuik, J.; Frassica, F.; "Engineered System Family #3: Information-enhanced Minimally Invasive Surgery," pp. 1-12; located at http://cisstweb.cs.jhu.edu/research/InfoEnhMIS/InfoEnhMISMain.htm; printed on Jul. 12, 2004.

Rochester Institute of Technoloy; "Introduction to Augmented Reality," pp. 1-12; located at http://www.se.rit.edu/~jrv/research/ar/introduction.html; printed on Jul. 12, 2004.

SIGGRAPH Emerging Technologies 1991-2002; "Interactive Paradigm, Technique," pp. 1-5; located at http://www.siggraph.org/~fujii/etech/s_interactive.html; bearing a date of Jul. 5, 2002; printed on Jul. 12, 2004.

SIGGRAPH Emerging Technologies 1991-2002; "Magic Morphin Mirror: Face-Sensitive Distortion and Exaggeration," pp. 1-2; located at http://siggraph.org./~jujii/etech/1997_190.html; bearing a date of Jul. 5, 2002; printed on Jul. 12, 2004.

Spohrer, J.C.; "Information in places," from vol. 38, allegedly of No. 4, 1999, Pervasive Computing; pp. 1-25; located at http://www.research.ibm.com/journal/sj/384/spohrer.html; printed on Jul. 12, 2004.

Sturm, Peter, "Mixing Catadioptric and Perspective Cameras," pp. 1-8, located at http://www.inrialpes.fr/movi/people/Sturm bearing a date of 2002 and printed on Sep. 1, 2004.

Tan, Kar-Han; Hua, Hong, Ahuja, Narenda "Multiview Panoramic Cameras Using Mirror Pyramids," accepted for publication in the IEEE Transactions on Pattern Analysis and Machine Intelligence journal, pp. 1-19 (+ cover sheet), printed on Sep. 1, 2004.

Taniguchi, Rin-Ichiro, "Real-Time Multiview Image Analysis and Its Application," pp. 1-8 printed on Sep. 1, 2004.

The Swiss Technorama Science Center, "Mirrors in Mind: Mirror, Mirror, on the Wall," pp. 1-12, located at http://www.technorama.ch/rentals/description.html printed on Sep. 1, 2004.

Traxtal; "What is Augmented Reality," pp. 1-2; located at http://www.traxtal.com/rd/rd_classroom_augmentedreality.htm; printed on Jul. 12, 2004.

U.S. Appl. No. 11/639,366, Jung et al.
U.S. Appl. No. 11/638,305, Allen et al.
U.S. Appl. No. 11/540,928, Allen et al.
U.S. Appl. No. 11/478,334, Allen et al.
PCT International Search Report; International App. No. PCT/US05/27410; Jan. 27, 2006.
PCT International Search Report; International App. No. PCT/US05/27250; May 2, 2006.
PCT International Search Report; International App. No. PCT/US05/27249; Apr. 21, 2006.

PCT International Search Report; International App. No. PCT/US05/27256; Apr. 21, 2006.
U.S. Appl. No. 12/220,671, Allen et al.
U.S. Appl. No. 12/154,694, Allen et al.
U.S. Appl. No. 11/982,731, Allen et al.
U.S. Appl. No. 11/982,396, Jung et al.
U.S. Appl. No. 11/982,326, Allen et al.
U.S. Appl. No. 11/726,114, Allen et al.
U.S. Appl. No. 10/951,002, Rinaldo Jr. et al.
U.S. Appl. No. 10/912,271, Rinaldo Jr. et al.
U.S. Appl. No. 10/910,421, Rinaldo Jr. et al.
PCT International Search Report; International App. No. PCT/US05/27411; Jul. 7, 2008; pp. 1-2.

* cited by examiner

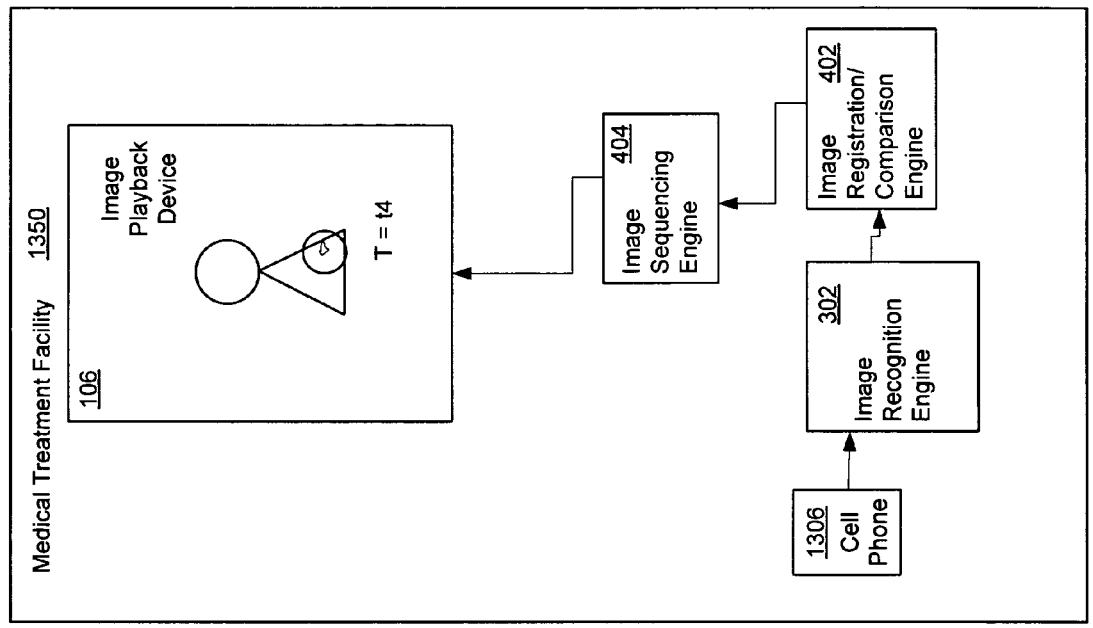
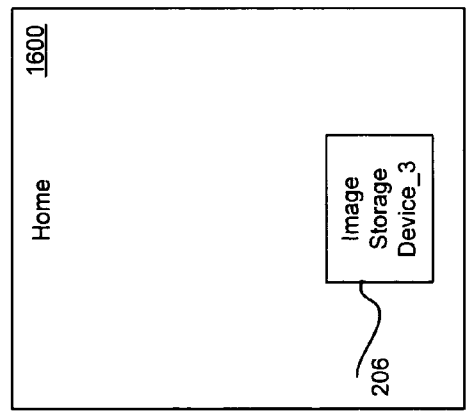
FIG. 17

TIME-LAPSING DATA METHODS AND SYSTEMS

CROSS-REFERENCE TO RELATED APPLICATIONS

The present application is related to, claims the earliest available effective filing date(s) from (e.g., claims earliest available priority dates for other than provisional patent applications; claims benefits under 35 USC § 119(e) for provisional patent applications), and incorporates by reference in its entirety all subject matter of the following listed application(s) (the "Related Applications"); the present application also claims the earliest available effective filing date(s) from, and also incorporates by reference in its entirety all subject matter of any and all parent, grandparent, great-grandparent, etc. applications of the Related Application(s). The United States Patent Office (USPTO) has published a notice to the effect that the USPTO's computer programs require that patent applicants reference both a serial number and indicate whether an application is a continuation or continuation in part. The present applicant entity has provided below a specific reference to the application(s) from which priority is being claimed as recited by statute Applicant entity understands that the statute is unambiguous in its specific reference language and does not require either a serial number or any characterization such as "continuation" or "continuation-in-part." Notwithstanding the foregoing, applicant entity understands that the USPTO's computer programs have certain data entry requirements, and hence applicant entity is designating the present application as a continuation in part of its parent applications, but expressly points out that such designations are not to be construed in any way as any type of commentary and/or admission as to whether or not the present application contains any new matter in addition to the matter of its parent application(s).

RELATED APPLICATIONS

1. For purposes of the USPTO extra-statutory requirements, the present application constitutes a continuation in part of currently United States patent application entitled TIME-LAPSING MIRROR, naming Paul G. Allen, Edward K. Y. Jung, Royce A. Levien, Mark A. Malamud, and John D. Rinaldo, Jr. as inventors, U.S. application Ser. No. 10/910,421 filed 2 Aug. 2004 now U.S. Pat. No. 7,283,106.

2. For purposes of the USPTO extra-statutory requirements, the present application constitutes a continuation in part of currently United States patent application entitled COSMETIC ENHANCEMENT MIRROR, naming Paul G. Allen, Edward K. Y. Jung, Royce A. Levien, Mark A. Malamud, and John D. Rinaldo, Jr. as inventors, U.S. application Ser. No. 10/912,271 filed 5 Aug. 2004 now U.S. Pat. No. 7,133,003.

3. For purposes of the USPTO extra-statutory requirements, the present application constitutes a continuation in part of currently co-pending United States patent application entitled MULTI-ANGLE MIRROR, naming Edward K. Y. Jung, Royce A. Levien, Mark A. Malamud, and John D. Rinaldo, Jr. as inventors, U.S. application Ser. No. 10/941,803 filed 15 Sep. 2004.

4. For purposes of the USPTO extra-statutory requirements, the present application constitutes a continuation in part of currently United States patent application entitled MEDICAL OVERLAY MIRROR, naming Paul G. Allen, Edward K. Y. Jung, Royce A. Levien, Mark A. Malamud, and John D. Rinaldo, Jr. as inventors, U.S. application Ser. No. 10/951,002 filed 27 Sep. 2004 now U.S. Pat. No. 7,259,731.

TECHNICAL FIELD

The present application relates, in general, to time-lapsing methods and systems.

SUMMARY

In one aspect, a system includes but is not limited to an image storage device configurable to store at least one historical image of at least a part of a patient; an image playback device (i) configurable to present responsive to a medical expert specification related to at least a part of an image of the patient and (ii) operably couplable to said image storage device; and an image sequencing engine (i) operably couplable to said image playback device and (ii) configurable to present at least a part of the at least one historical image in a time-lapse context. In addition to the foregoing, other system aspects are described in the claims, drawings, and text forming a part of the present application.

In one aspect, a method includes but is not limited to accepting input related to at least one remotely-captured patient image; and presenting to a medical expert one or more historical images related to at least a part of the at least one remotely-captured patient image in a time-lapse context. In addition to the foregoing, other method aspects are described in the claims, drawings, and text forming a part of the present application.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

In one aspect, a method includes but is not limited to recognizing a medical indicator; and presenting at least a part of one or more remotely-captured images in response to the recognized medical indicator. In addition to the foregoing, other method aspects are described in the claims, drawings, and text forming a part of the present application.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

In one aspect, a method includes but is not limited to accepting input of at least a part of a remotely-captured image of a mirror; and presenting to a medical expert one or more historical images related to at least a part of the remotely-captured image of the mirror. In addition to the foregoing, other method aspects are described in the claims, drawings, and text forming a part of the present application.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

In one aspect, a method includes but is not limited to accepting input of at least a part of a remotely-captured image of a wireless device; and presenting to a medical expert one or more historical images related to at least a part of the remotely-captured image of the wireless device.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

In addition to the foregoing, various other method and/or system aspects are set forth and described in the text (e.g., claims and/or detailed description) and/or drawings of the present application.

The foregoing is a summary and thus contains, by necessity, simplifications, generalizations and omissions of detail; consequently, those skilled in the art will appreciate that the summary is illustrative only and is NOT intended to be in any way limiting. Other aspects, inventive features, and advantages of the devices and/or processes described herein, as defined solely by the claims, will become apparent in the detailed description set forth herein.

BRIEF DESCRIPTION OF THE FIGURES

FIG. 17 depicts a cell phone 1306 wirelessly accessing historical images of image storage device_3 206, such as over a cellular network.

The use of the same symbols in different drawings typically indicates similar or identical items.

DETAILED DESCRIPTION

Figure 1:
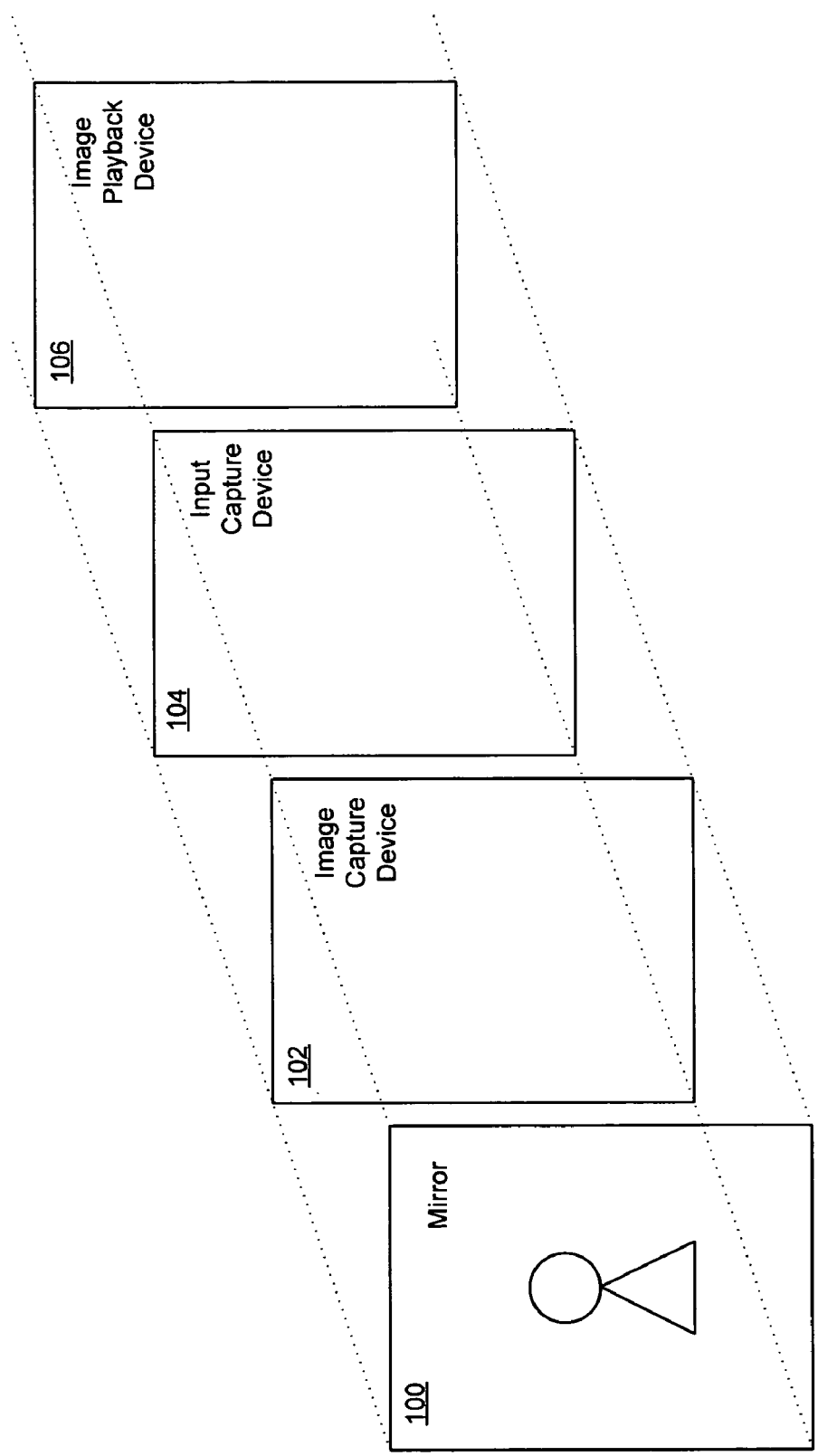
FIG. 1 shows a partial view of a system that may serve as an illustrative environment of and/or for subject matter technologies.

With reference to the figures, and with reference now to FIG. 1, shown is a partial view of a system that may serve as an illustrative environment of and/or for subject matter technologies. Depicted are mirror 100, image capture device 102, input capture device 104, and image playback device 106. In one exemplary implementation, mirror 100 can be a plane mirror, a convex mirror, and/or a concave mirror. Examples of such mirrors may include bathroom, hall, and/or handheld mirrors. In another exemplary implementation, mirror 100 can be a partially silvered mirror. In some exemplary implementations, mirror 100 can be a physical mirror. In other exemplary implementations, mirror 100 can be a digital mirror and/or a projection mirror. In yet other implementations, mirror 100 can be a combination of one or more physical mirrors and/or one or more digital mirrors and/or one or more projection mirrors. In some implementations, image playback device 106 may present various types of time-lapse information in addition or in the alternative to image information, such as height and/or weight information. In some implementations, presentations of information may be in the form of various modalities including but not limited to graphs, tables, audio (speech, music, sound), text, email (e.g. a weekly digest), et cetera.

Continuing to refer to FIG. 1, illustrated is image playback device 106 proximate to mirror 100. One exemplary implementation of image playback device 106 proximate to mirror 100 includes but is not limited to image playback device 106 integral with physical mirror 100. Another exemplary implementation of image playback device 106 proximate to mirror 100 includes but is not limited to image playback device 106 operably coupled with physical mirror 100 (e.g., as used herein, proximate may mean operationally proximate—able to work and interact together either directly or through intermediate components—as well as and/or in addition to physically proximate and/or mechanically proximate). Yet another exemplary implementation of image playback device 106 proximate to mirror 100 includes but is not limited to image playback device 106 in physical communication with physical mirror 100. One exemplary implementation of image playback device 106 in physical communication with physical mirror 100 includes but is not limited to image playback device 106 connected with a frame connected with said physical mirror 100. In some implementations, image playback device 106 can be a light generation device (e.g., a plasma display and/or a liquid crystal display), an image presentation device (e.g., a direct projection to the eye retinal display), and/or a laser device (e.g., a laser diode device), overlays (e.g. onto templates on a medical expert's computer or other device), e-paper, a printout, etc.

Figure 2:
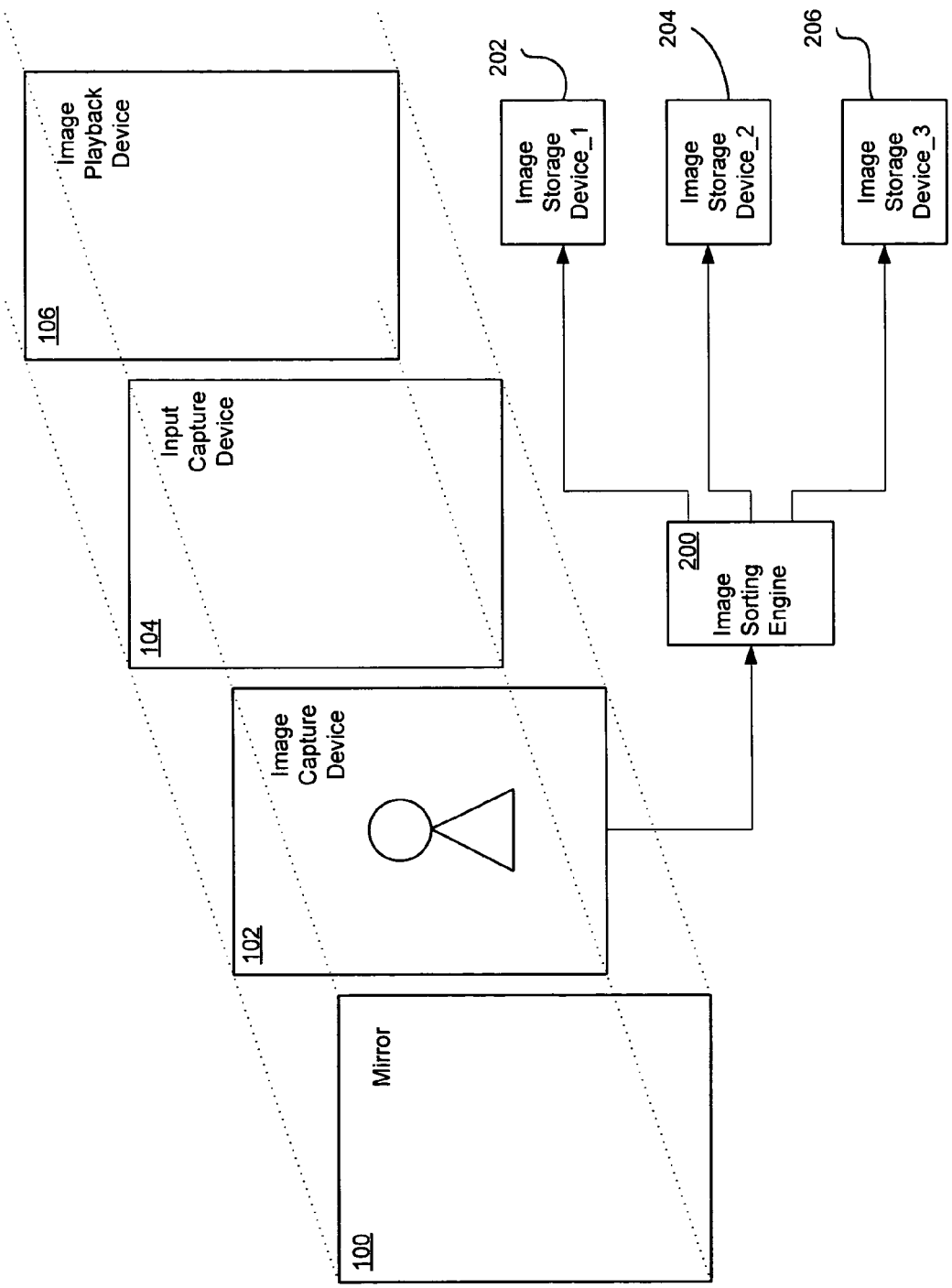
FIG. 2 depicts a partial view of a system that may serve as an illustrative environment of and/or for subject matter technologies.

Referring now to FIG. 2, depicted is a partial view of a system that may serve as an illustrative environment of and/or for subject matter technologies. Illustrated is that image sorting engine 200 interfaces with image capture device 102. Shown is that image sorting engine 200 interfaces with image storage device_1 202, image storage device_2 204, and image storage device_3 206. In one exemplary implementation, image sorting engine 200 receives images from image capture device 102 and sorts the received images into one or more of image storage device_1 202, image storage device_2 204, and image storage device_3 206 based on pattern recognition algorithms. For example, in an implementation where image capture device 102 is capturing three-dimensional (3-D) images of a human subject, image sorting engine 200 may utilize 3-D image processing routines to sort various recognized captured images into image storage device_1 202, image storage device_2 204, and image storage device_3 206 (e.g., where images of a first person are sorted to image storage device_1 202, images of a second person are sorted to image storage device_2 204, and images of a third person are sorted to image storage device_3 206). Those skilled in the art will appreciate that, as used herein, sorting can include categorization, ordering, and/or other operations such as those described herein.

Continuing to refer to FIG. 2, in one implementation, image capture device 102 can include at least one image representation device located to capture a field of view of mirror 100. For example, an active photo-detector array completely and/or partially in identity with a display portion of mirror 100 or a lensed image capture system is oriented such that it could capture all or part of an image reflected from mirror 100. In another exemplary implementation, image capture device 102 can include at least two image representation devices located to capture a field of view of mirror 100. For example, two or more camera systems positioned to capture stereo imagery such that 3-D imaging techniques may be applied. The image capture devices described herein can be positioned substantially anywhere an image of mirror 100 can be captured, such as behind mirror 100 in order to catch transmitted images through a partially silvered mirror, to the sides and/or above and/or below a mirror, and/or positioned and/or oriented to the front of a mirror in order to record images reflected from a mirror. In some implementations, the image capture devices may also be positioned such that they reside behind where a user would be expected to stand when viewing mirror 100.

Figure 3:
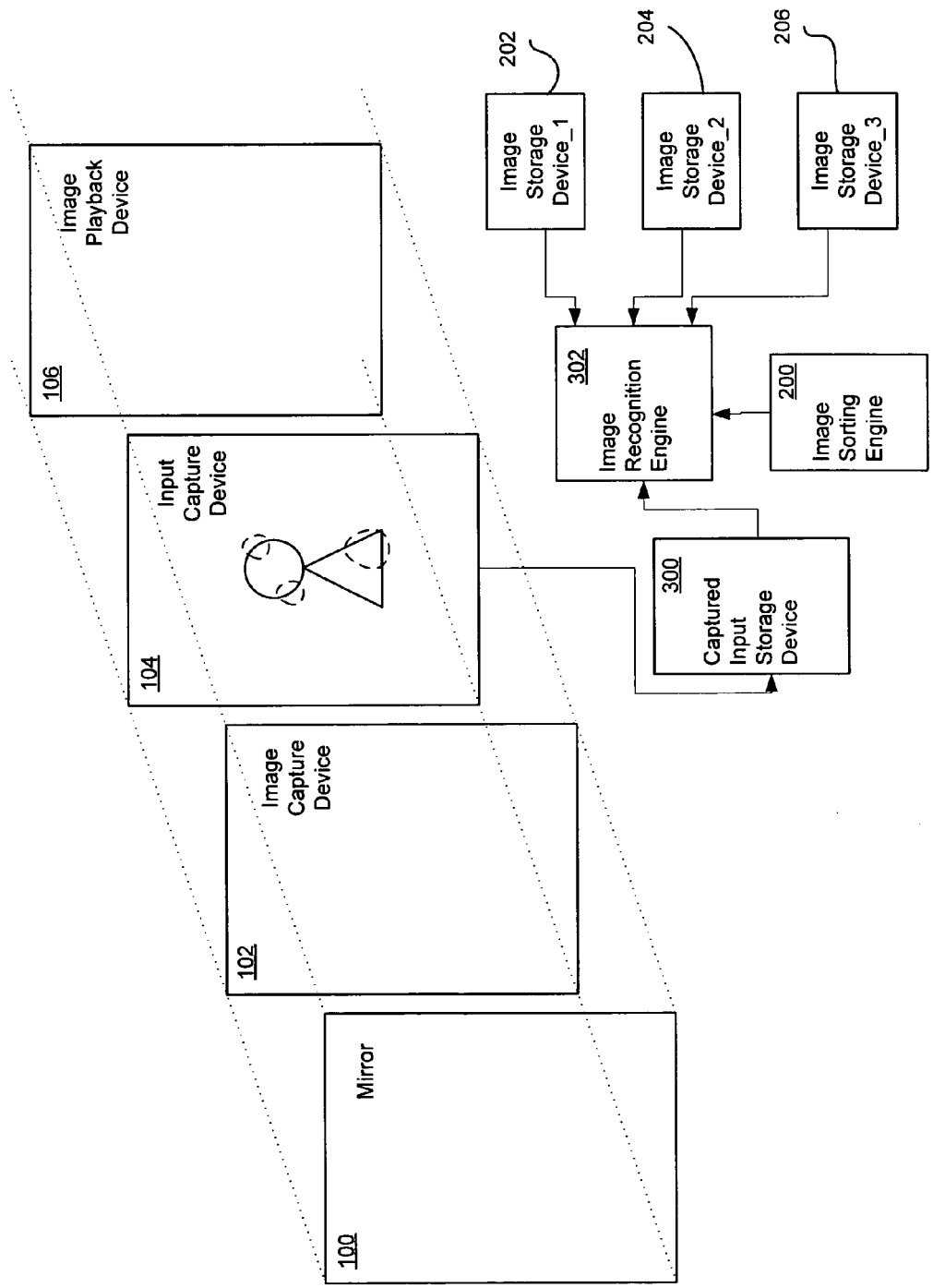
FIG. 3 illustrates a partial view of a system that may serve as an illustrative environment of and/or for subject matter technologies.

With reference now to FIG. 3, illustrated is a partial view of a system that may serve as an illustrative environment of and/or for subject matter technologies. Shown is captured input storage device 300 exchanging signals with input capture device 104. Depicted is image recognition engine 302 exchanging signals with captured input storage device 300, image sorting engine 200, image storage device_1 202, image storage device_2 204, and image storage device_3 206. In one exemplary implementation, a user (e.g., a human user) touches and/or circles a region of an image in mirror 100 and asks that the system show a time-lapse presentation of the region over some interval of time. For example, a human user touching a skin lesion on his/her image and asking that the system show the mole over the last three months. In response, in one implementation captured input storage device 300 captures both the region of the image touched as well as the request for the time-lapse presentation of the mole (in some implementations, the request is typed such as via touch screen entry to a menu driven system, while in other implementations, the request is spoken such as via voice recognition input driven system). Thereafter, in one implementation, image recognition engine 302 interacts with image sorting engine 200 to determine where images associated with the person whose input has been captured are stored. For example, if the person in the mirror's previously captured images had been stored in image storage device_3 206, then image sorting engine 200 would inform image recognition engine 302 of that fact. Thereafter, image recognition engine 302 would know the storage location of that person's image.

Figure 4:
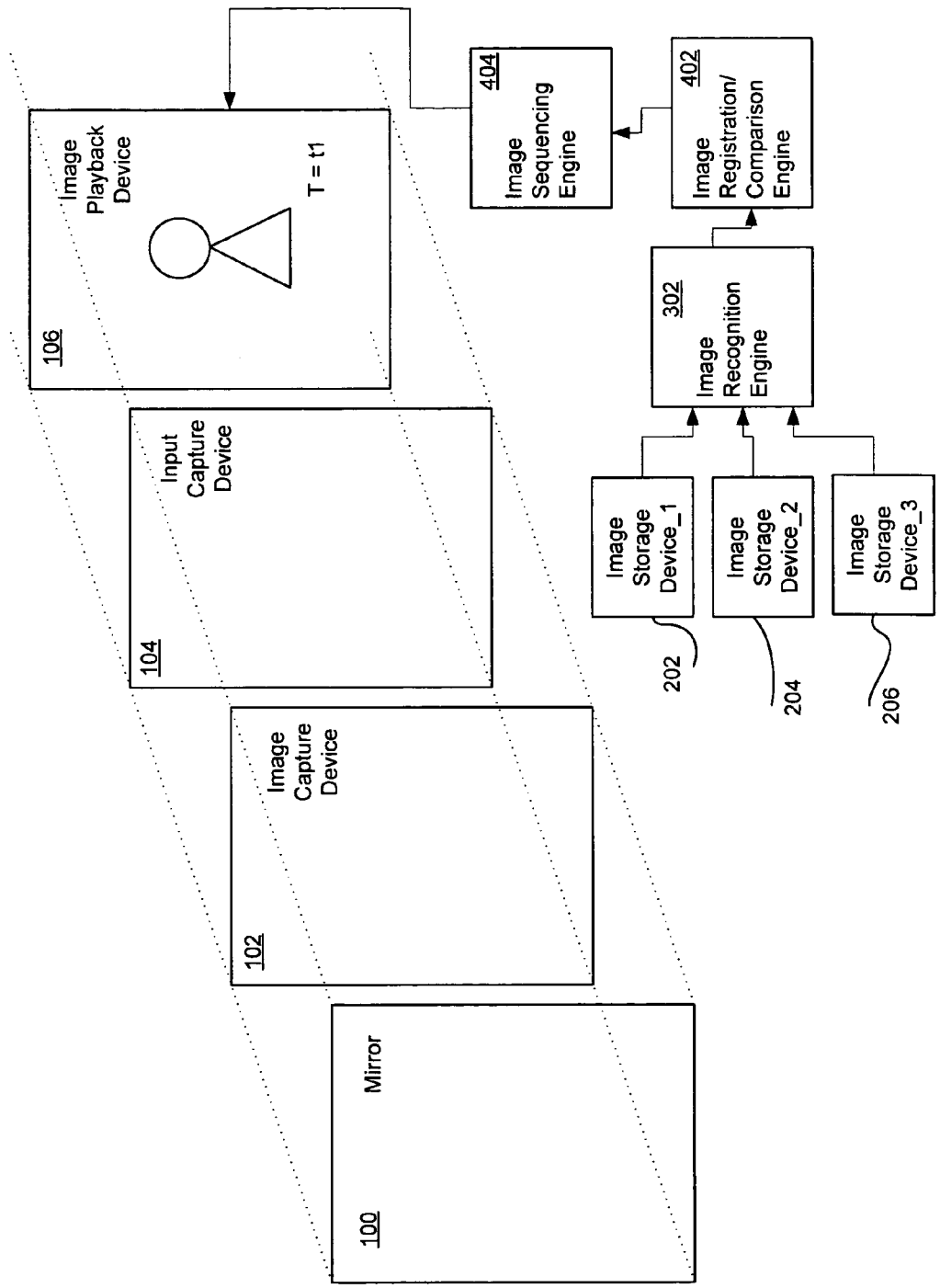
FIG. 4 shows a partial view of a system that may serve as an illustrative environment of and/or for subject matter technologies.

Referring now to FIG. 4, shown is a partial view of a system that may serve as an illustrative environment of and/or for subject matter technologies. Depicted is image recognition engine 302 interfaced with image sorting engine 200, image storage device_1 202, image storage device_2 204, and image storage device_3 206. Illustrated is image recognition engine 302 interfaced with image registration/comparison engine 402. Shown is image registration/comparison engine 402 interfaced with image sequencing engine 404. In one exemplary implementation, image recognition engine 302 retrieves time-sequenced images from one or more of image storage device_1 202, image storage device_2 204, and image storage device_3 206. Thereafter, image registration/comparison engine 402 uses some relatively stable image feature(s), such as anatomical landmarks (e.g., bony regions or a center part of some defined anatomical feature), to encompass and or localize a region of interest where some feature of interest resides, to provide proper alignment. Image sequencing engine 404 then presents the aligned images in a time sequenced fashion such that the changes in the region of interest can be viewed over time. For instance, a time-lapse presentation of how a mole has grown over the last few months.

In some implementations, instead of or as an addition to the foregoing, image registration/comparison engine 402 compares a specified feature (e.g., hair length or jowl size) against a reference value and presents information (e.g., an alert) when the specified feature exceeds the reference value by some defined amount. As a specific example, a user might instruct the system to alert her if her hair has grown more than 8 millimeters beyond some reference length. If her hair did exceed the threshold beyond the reference length, the system would present a display indicating that event, and perhaps suggesting that a haircut was needed.

Figure 5:
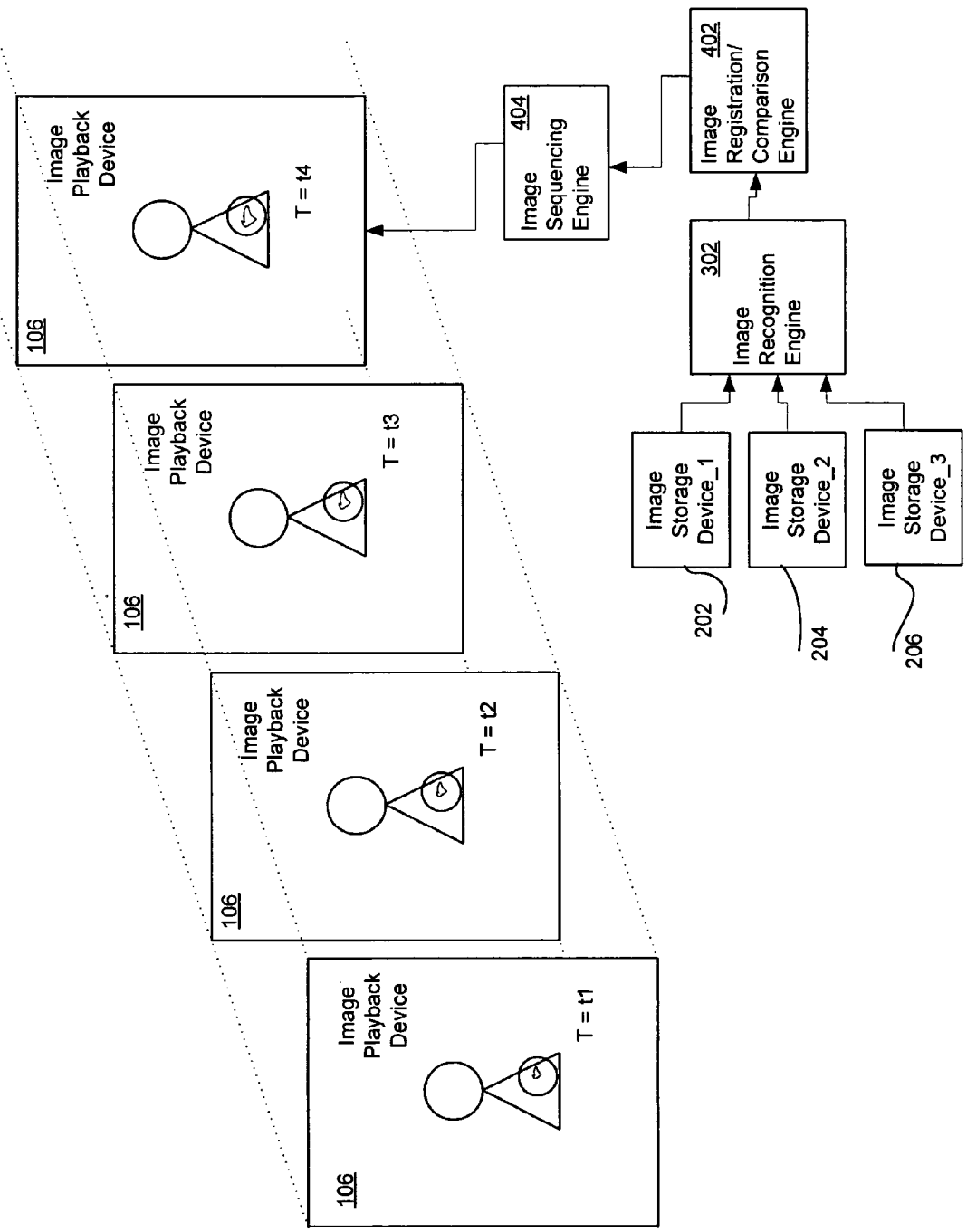
FIG. 5 depicts a partial view of a system that may serve as an illustrative environment of and/or for subject matter technologies.

With reference now to FIG. 5, depicted is a partial view of a system that may serve as an illustrative environment of and/or for subject matter technologies. Illustrated is the system presenting four (4) time sequenced views showing the growth of lesion within a skin region over time. Depicted is that the lesion is dark with an irregular border and growing, such as, for example, a melanoma region. Other things could be like depicted, like hair length, jowl size, etc.

Following are a series of flowcharts depicting implementations of processes. For ease of understanding, the flowcharts are organized such that the initial flowcharts present implementations via an overall "big picture" viewpoint and thereafter the following flowcharts present alternate implementations and/or expansions of the "big picture" flowcharts as either sub-steps or additional steps building on one or more earlier-presented flowcharts. Those having skill in the art will appreciate that the style of presentation utilized herein (e.g., beginning with a presentation of a flowchart(s) presenting an overall view and thereafter providing additions to and/or further details in subsequent flowcharts) generally allows for a rapid and easy understanding of the various process implementations.

Figure 6:
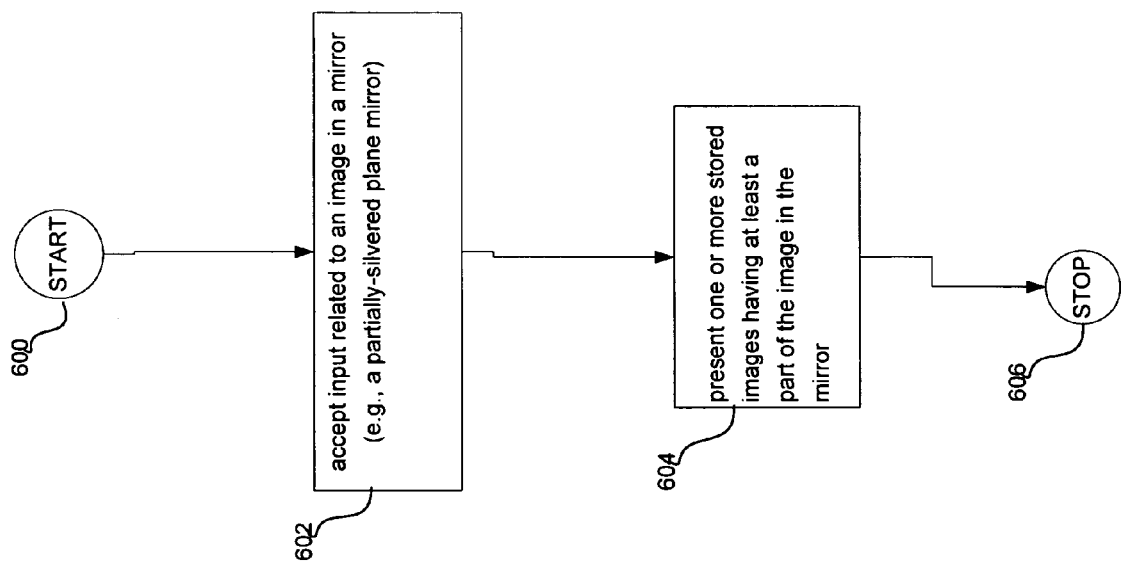
FIG. 6 illustrates a high-level logic flowchart of a process.

Referring now to FIG. 6, illustrated is a high-level logic flowchart of a process. Method step 600 shows the start of the process. Method step 602 shows accepting input related to an image in a mirror (e.g., via captured input storage device 300 and/or its supporting components). Method step 604 depicts presenting one or more stored images having at least a part of the image in the mirror (e.g., such as shown/described in relation to FIG. 5). Method step 606 shows the end of the process. Those skilled in the art will appreciate that, in some implementations, the "at least a part of the image" can include but is not limited to a recognized region of an image or a recognized anchor point associated with an image which will provide the ability to do presentation on regions that both are and are not readily visually coordinated with an original field of view of a mirror. For example, in a handheld mirror implementation, a user might zoom in on a region of an image and then ask to see a time-lapse sequence of images representative of changes in that zoomed-in region, such that the zoomed-in region is not readily visually coordinated with the original unzoomed field of view of the mirror. The inventors point out that those skilled in the art will appreciate that while the zoomed-in region might not be easily visually coordinated with the unzoomed field of view, in some implementations the use of anchor points will allow coordination between the zoomed and unzoomed views. In addition, the inventors further point out that while examples set forth herein focus on anatomy and/or anatomical change for the sake of clarity, the systems described herein can actually track and/or show a time lapse of substantially any object that may be reflected in the mirror. For instance, a person being able to use her cell phone in an airport bathroom to send an image of here stools in the toilet so that subsequently a medical expert could call up a history of her stools would in fact constitute an image "of" that person, or "of at least a part of that person," as such words/phrases are used herein.

Figure 7:
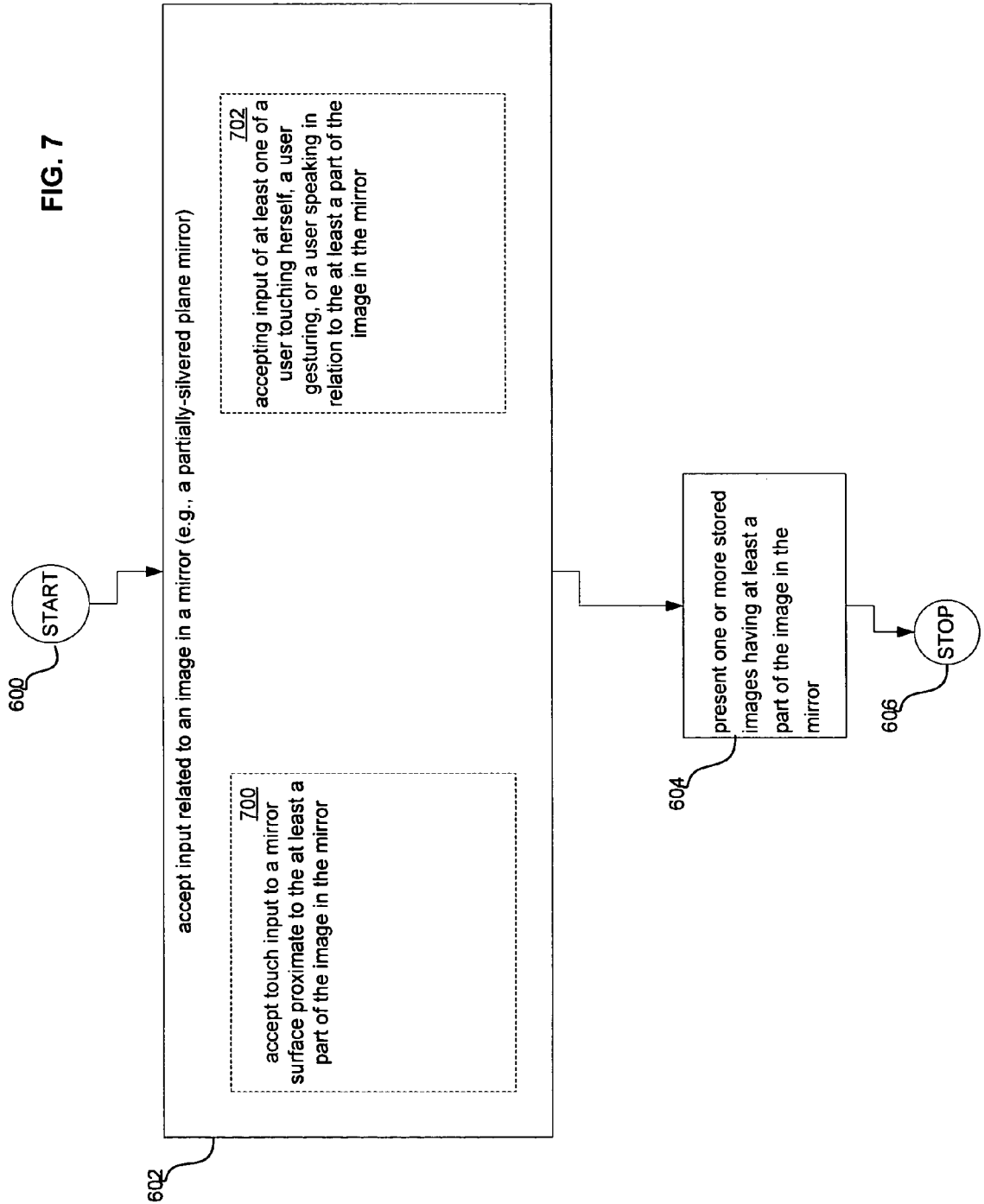
FIG. 7 shows a high-level logic flowchart depicting alternate implementations of the high-level logic flowchart of FIG. 6.

With reference now to FIG. 7, shown is a high-level logic flowchart depicting alternate implementations of the high-level logic flowchart of FIG. 6. Depicted is that in various alternate implementations, method step 602 includes method step 700 and/or method step 702. Method step 700 shows accepting touch input to a mirror surface proximate to the at least a part of the image in the mirror (e.g., via input capture device 104 capturing input when a user's finger is proximate to an image in mirror 100). Method step 702 depicts accepting input of at least one of a user touching herself, a user gesturing, or a user speaking in relation to the at least a part of the image in the mirror (e.g., via input capture device 104 capturing input when a user's gestures or pointing relative to at least a part of an image in mirror 100 and/or the user speaking a command in relation to at least a part of an image in mirror 100).

Figure 8:
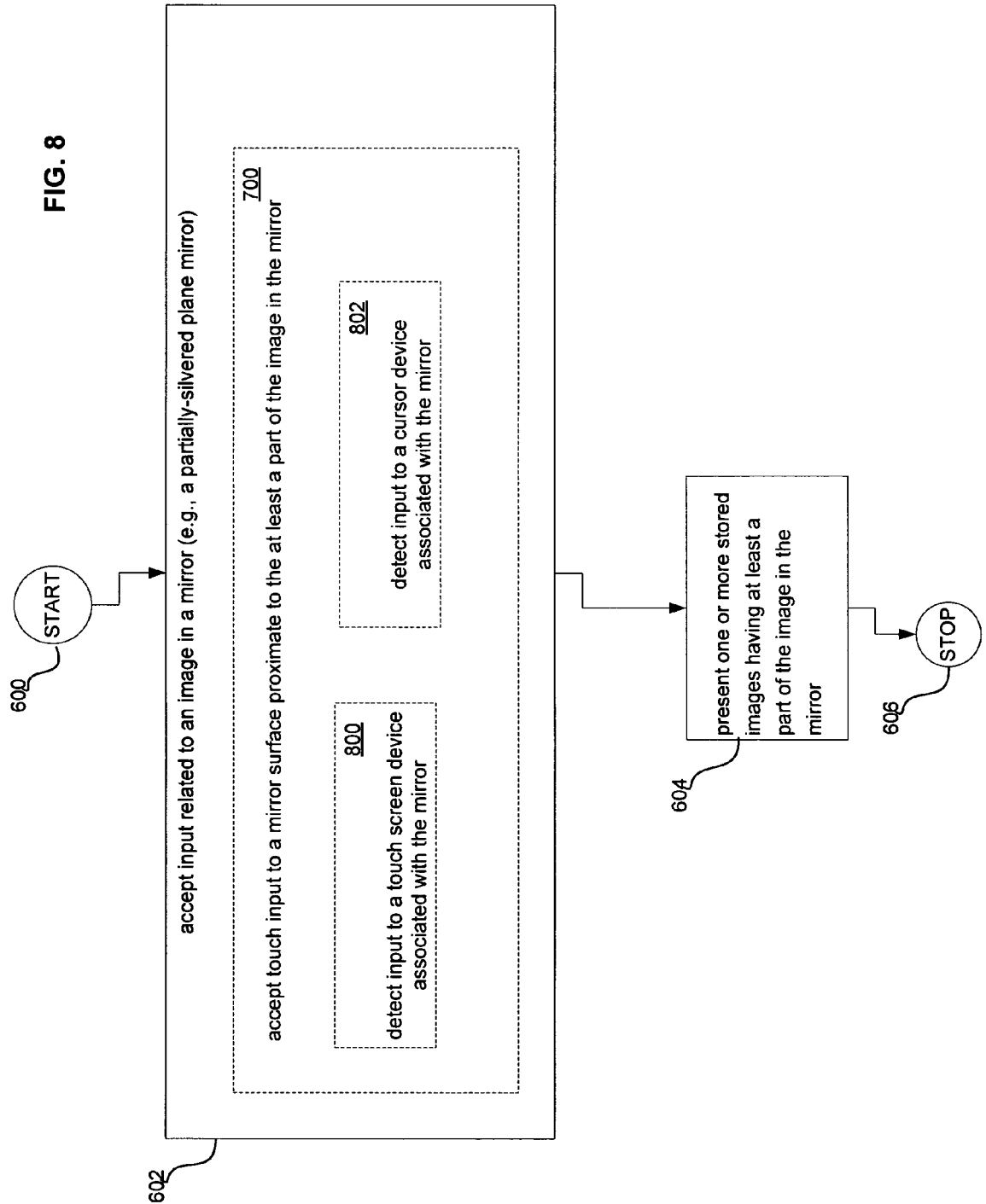
FIG. 8 depicts a high-level logic flowchart depicting alternate implementations of the high-level logic flowchart of FIG. 7.

Referring now to FIG. 8, depicted is a high-level logic flowchart depicting alternate implementations of the high-level logic flowchart of FIG. 7. Depicted is that in one alternate implementation, method step 700 includes method step 800 and/or method step 802. Method step 800 shows detecting input to a touch screen device associated with the mirror (e.g. via mirror 100 and/or input capture device 104 and/or one or more of their supporting components). Method step 802 depicts detecting input to a cursor device associated with the mirror (e.g. via mirror 100 and/or input capture device 104 and/or one or more of their supporting components).

Figure 9:
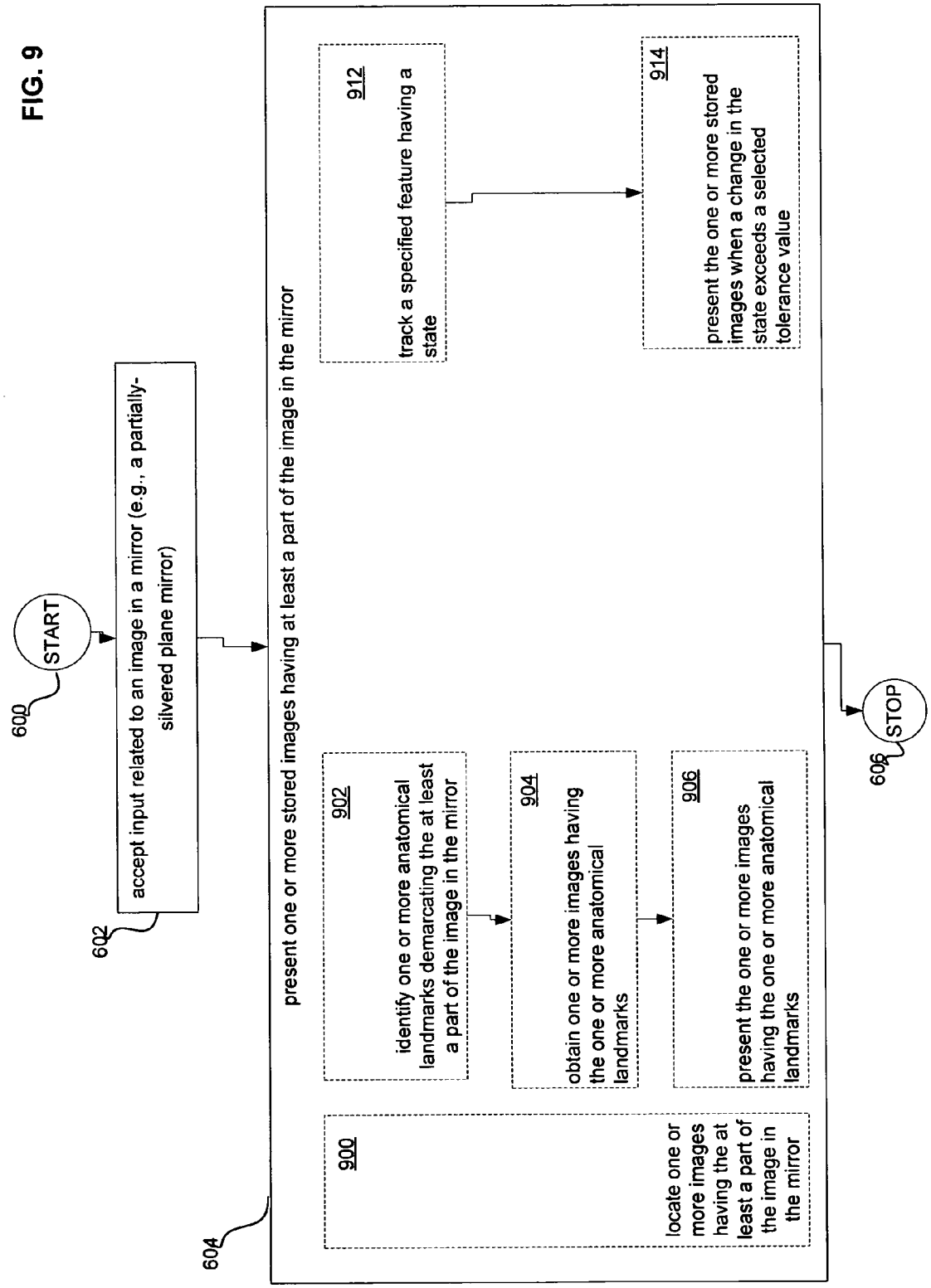
FIG. 9 illustrates a high-level logic flowchart depicting alternate implementations of the high-level logic flowchart of FIG. 6.

With reference now to FIG. 9, illustrated is a high-level logic flowchart depicting alternate implementations of the high-level logic flowchart of FIG. 6. Depicted is that in various alternate implementations, method step 604 includes method step 900, and/or method steps 902-906, and/or method steps 912-914. Method step 900 shows one alternate implementation of locating one or more images having the at least a part of the image in the mirror. For example, locating the one or more images via image sorting engine 200, captured input storage device 300, image recognition engine 302, and/or one or more of image storage devices 202-206.

Continuing to refer to FIG. 9, method steps 902-906 depict another alternate embodiment. Method step 902 illustrates identifying one or more anatomical landmarks demarcating the at least a part of the image in the mirror (e.g., via image sorting engine 200 and/or image recognition engine 302). Method step 904 shows obtaining one or more images having the one or more anatomical landmarks (e.g., via image recognition engine 302 and/or image registration/comparison engine 402). Method step 906 depicts presenting the one or more images having the one or more anatomical landmarks (e.g., via image playback device 106 and/or image sequencing engine 404).

Continuing to refer to FIG. 9, method steps 912-914 illustrate yet another alternate embodiment. Method step 912 shows tracking a specified feature having a state (e.g., via image registration/comparison engine 402 and/or its supporting components). Method step 914 depicts presenting the one or more stored images when a change in the state exceeds a selected tolerance value (e.g., via image registration/comparison engine 402 and/or image sequencing engine 404 and/or their supporting components).

Figure 10:
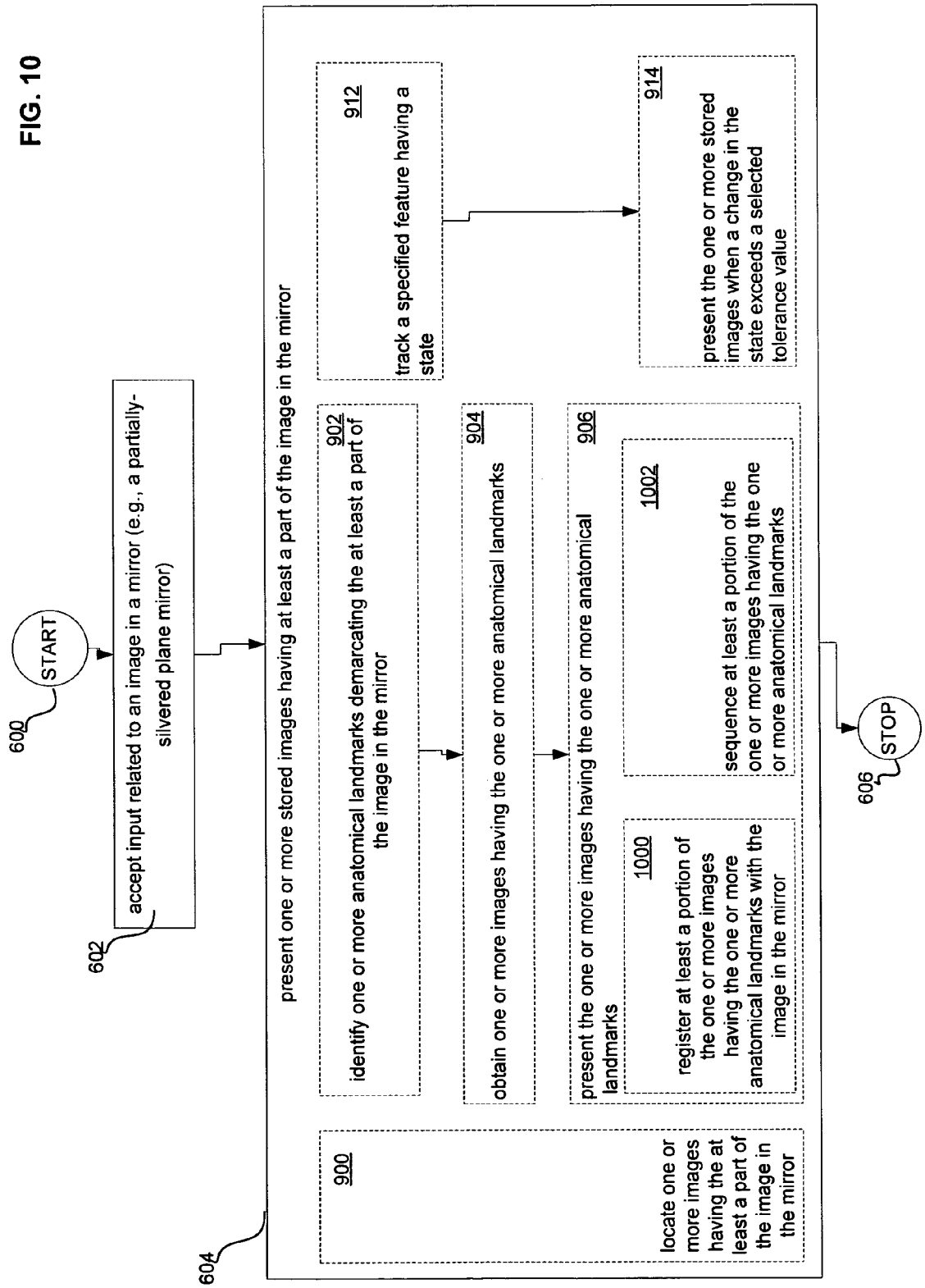
FIG. 10 shows a high-level logic flowchart depicting alternate implementations of the high-level logic flowchart of FIG. 9.

Referring now to FIG. 10, shown is a high-level logic flowchart depicting alternate implementations of the high-level logic flowchart of FIG. 9. Depicted is that in various alternate implementations, method step 906 includes method step 1000 and/or method step 1002. Method step 1000 illustrates registering at least a portion of the one or more images having the one or more anatomical landmarks with the image in the mirror (e.g., via image registration/comparison engine 402). Method step 1002 shows sequencing at least a portion of the one or more images having the one or more anatomical landmarks (e.g., via image sequencing engine 404).

Figure 11:
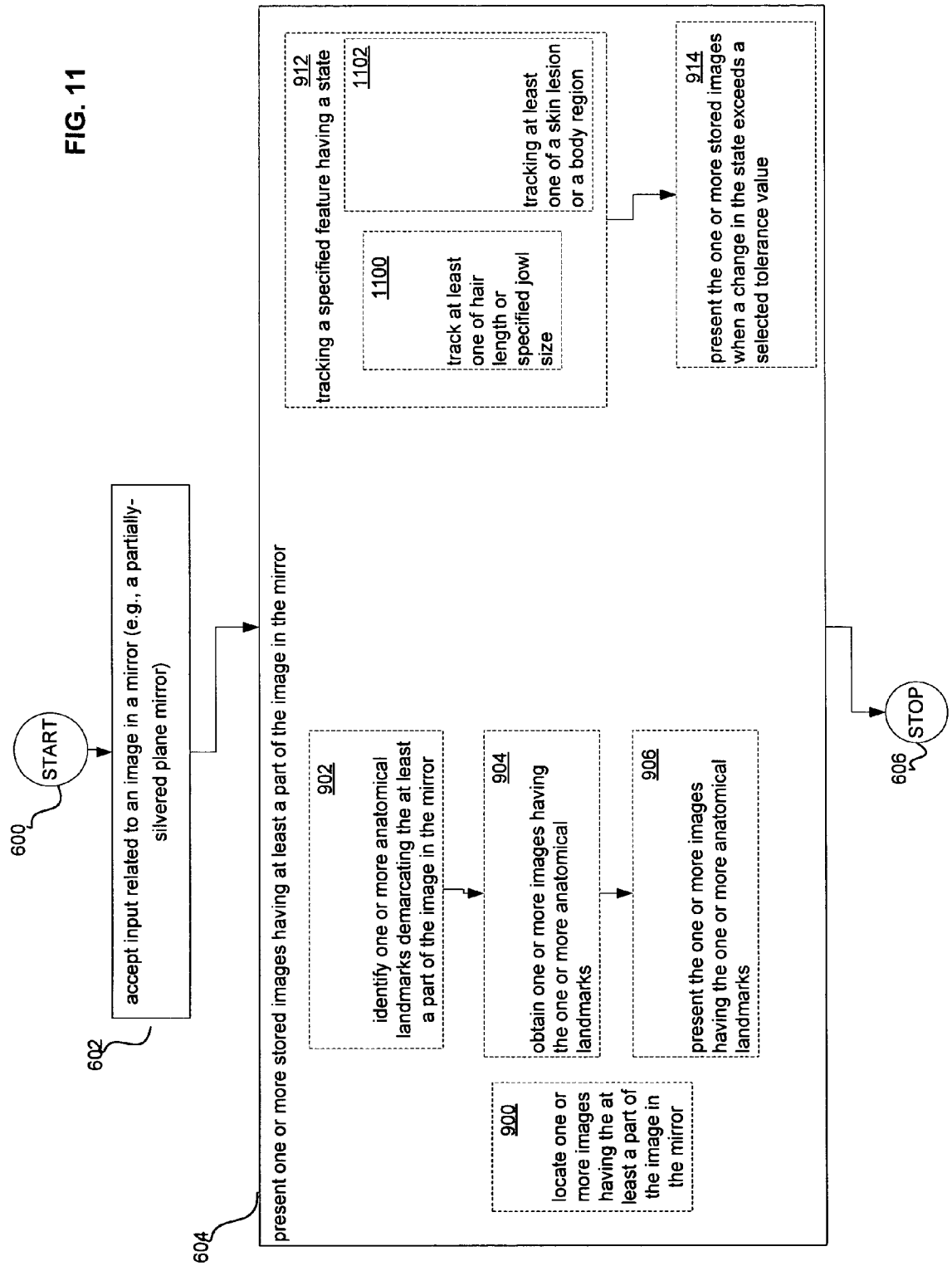
FIG. 11 depicts a high-level logic flowchart depicting alternate implementations of the high-level logic flowchart of FIG. 9.

With reference now to FIG. 11, depicted is a high-level logic flowchart depicting alternate implementations of the high-level logic flowchart of FIG. 9. Illustrated is that in various alternate implementations, method step 912 includes method step 1100 and/or method step 1102. Method step 1100 illustrates tracking at least one of hair length or specified jowl size (e.g., via image registration/comparison engine 402 and/or its supporting components). Method step 1102 shows tracking at least one of a skin lesion or a body region (e.g., via image recognition engine 302 and/or image registration/comparison engine 402 and/or their supporting components), which the inventors point out is helpful in a handheld mirror implementation.

Figure 12:
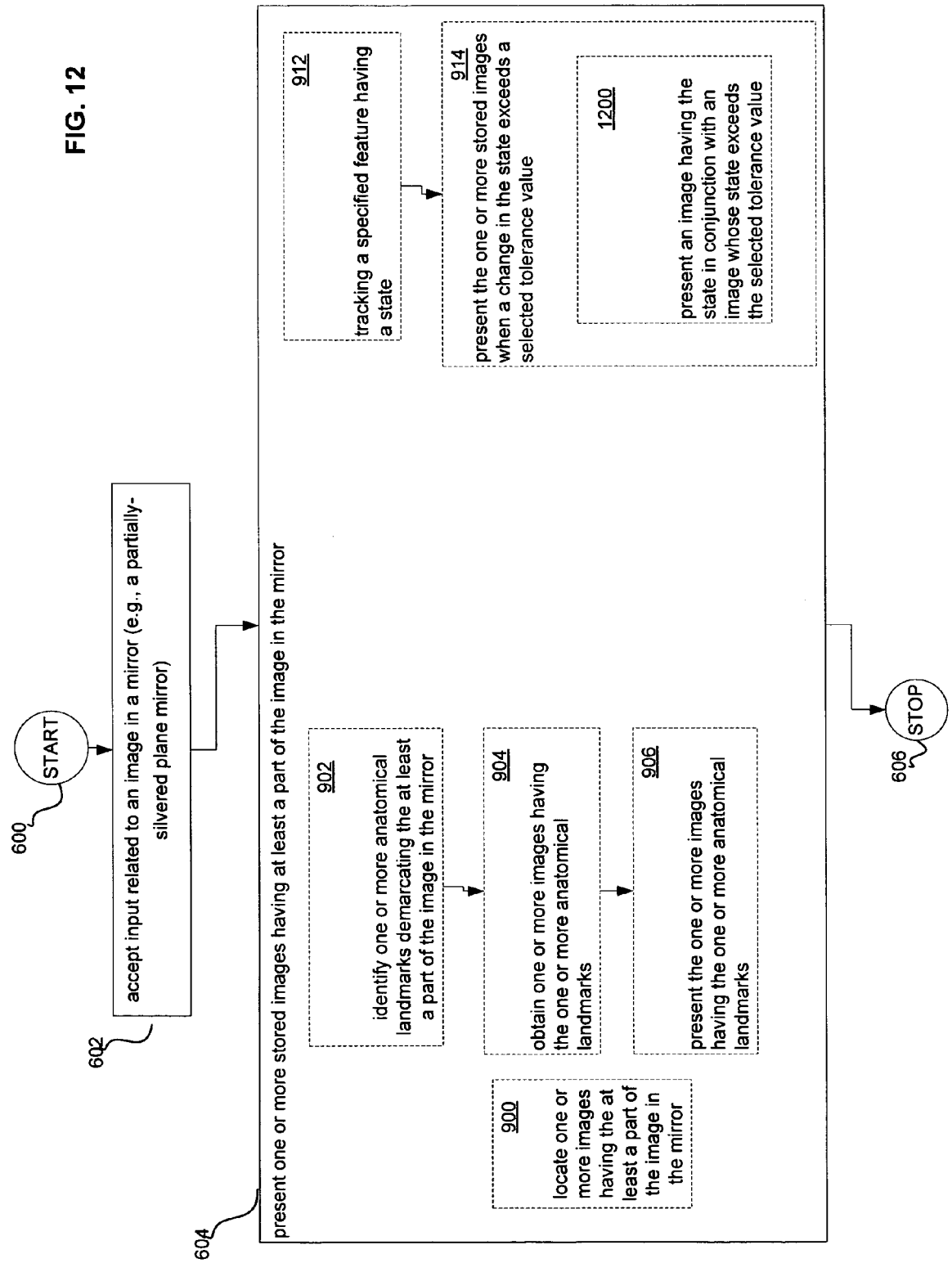
FIG. 12 illustrates a high-level logic flowchart depicting an alternate implementation of the high-level logic flowchart of FIG. 9.

Referring now to FIG. 12, illustrated is a high-level logic flowchart depicting an alternate implementation of the high-level logic flowchart of FIG. 9. Shown is that in one alternate implementation, method step 914 includes method step 1200. Method step 1200 shows presenting an image having the state in conjunction with an image whose state exceeds the selected tolerance value (e.g., via image recognition engine 302 and/or image registration/comparison engine 402 and/or image sequencing engine 404 and/or their supporting components).

Figure 13:
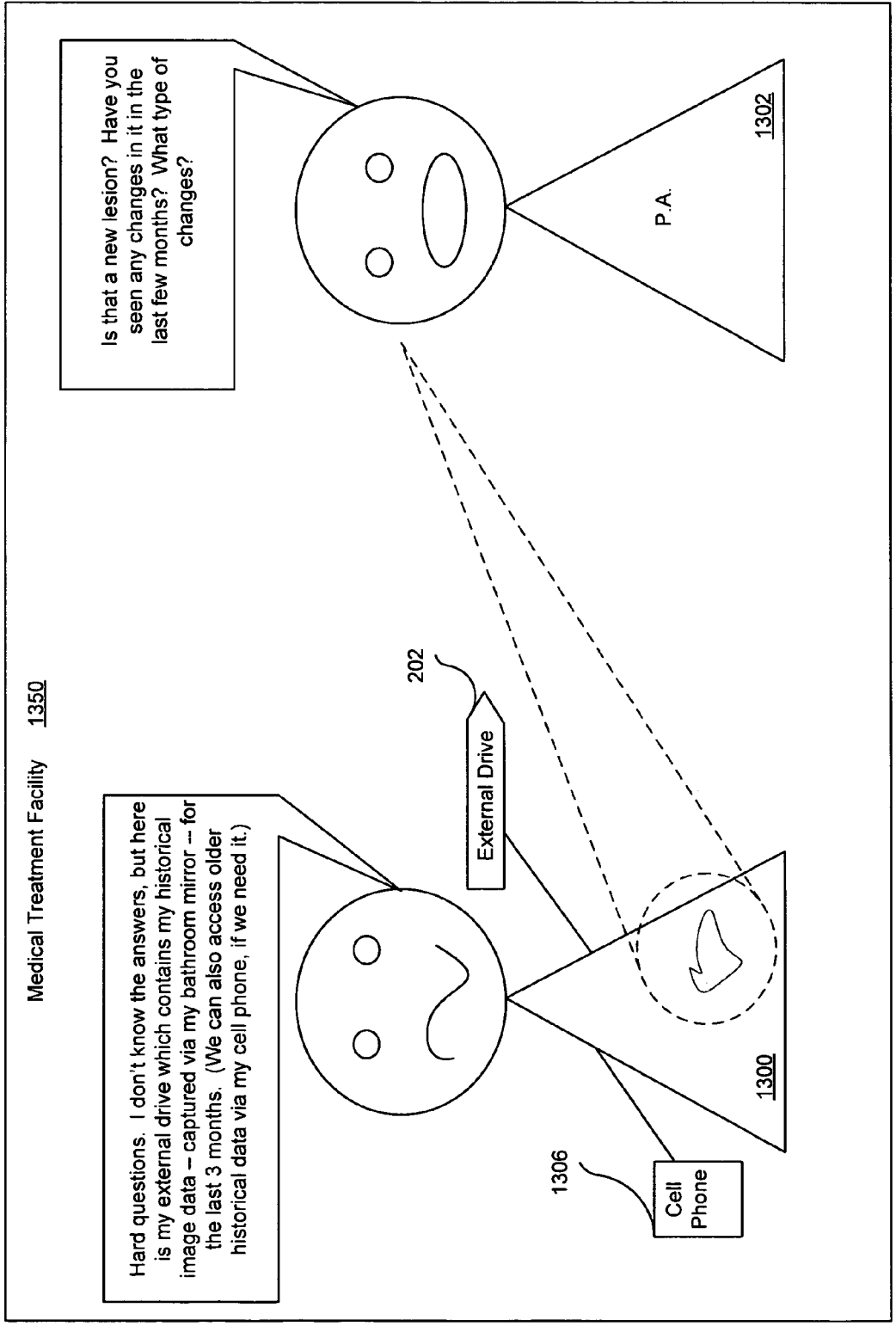
FIG. 13 shows a pictographic representation of a dialog between patient 1300 and physician's assistant ("P.A.") 1302 that is transpiring in medical treatment facility 1350 (e.g., a clinic, hospital, physician's office, hospice, a home hospice setting, etc.).

With reference now to FIG. 13, shown is a pictographic representation of a dialog between patient 1300 and physician's assistant ("P.A.") 1302 that is transpiring in a medical treatment facility 1350 (e.g., a clinic, hospital, physician's office, hospice, a home hospice setting, etc.). Depicted is that physician's assistant 1302 is visually examining patient 1300's skin lesion and asking questions related thereto. Specifically illustrated is that physician's assistant 1302 is asking whether the lesion is new, whether the patient has seen any changes in the skin lesion in the last few months, and, if so, what type of changes. Depicted is that patient 1300 is responding that he does not remember, but that he has historical image data of his torso for at least the last 3 months on external drive 1304 which is one exemplary implementation of image storage device 202, 204, and/or 206 described elsewhere herein, and which may be any suitable commercially available external drive (e.g., a USB flash drive, a micro hard drive, an EEPROM, etc.). Further depicted is that the patient is also responding that older data can be accessed from other remote storage through patient 1300's cell phone 1306. FIG. 13 is illustrative of the more general scenario wherein a medical expert might desire historical data related to a medical indicator (e.g., a condition).

Figure 14:
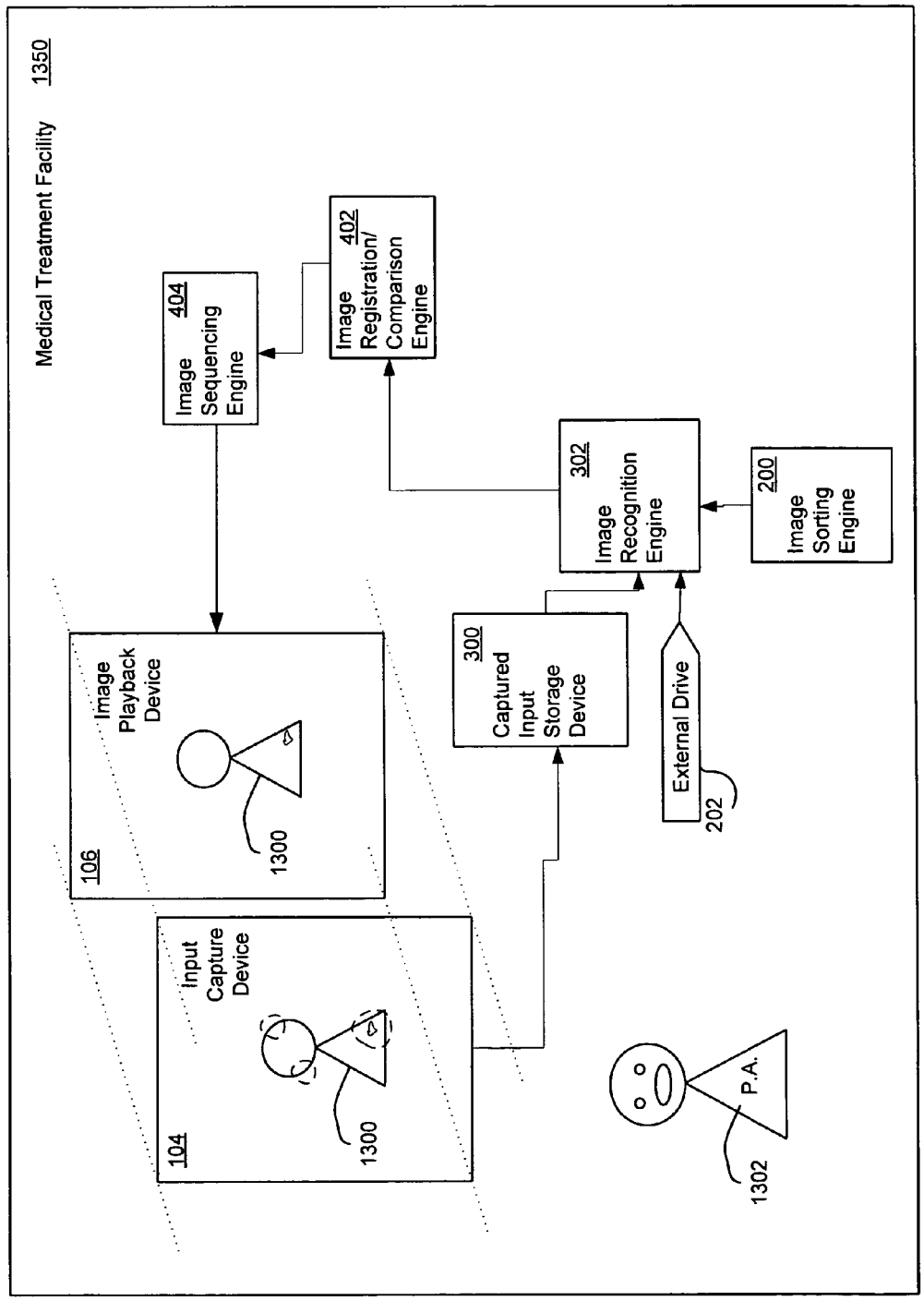
FIG. 14 depicts a medical treatment facility 1350 containing a system having components analogous to those described in relation to FIGS. 3,4, and/or other figures elsewhere herein.

Referring now to FIG. 14, depicted is medical treatment facility 1350 containing a system having components analogous to those described in relation to FIGS. 3, 4, and/or other figures elsewhere herein. Illustrated is image sequencing engine 404 presenting an image of patient 1300 through image playback device 106. In one implementation, the presented image is a remotely-captured historical image of patient 1300 gleaned from external drive 202, while in another implementation the presented image is a proximately captured image, such as might be captured by a camera of medical treatment facility 1350 or with a cell phone camera such as might be carried by patient 1300 and/or physician's assistant 1302.

Depicted is input capture device 104 accepting input indicative of medical indicators resident within or on the image of patient 1300 (e.g., accepting input specifying a portion of the image containing a suspicious-looking lesion). In one implementation, the input is generated by a robotic entity (e.g., an artificially intelligent medical expert system) in response to a robotic entity within an image recognition engine detecting the medical indicator resident within or on the image. In one implementation, the robotic entity uses commercially available medical image recognition logic. In another implementation, the robotic entity uses commercially available medical image recognition logic in conjunction with historical images of the medical indicator to detect changes in the historical images indicative of a medical condition (e.g., a skin lesion growing larger and/or darker). In one implementation, the input is received from a human medical expert (e.g., physician's assistant 1302) using one or more input devices such as a mouse, cursor, laser pointer, gesture, voice recognition, etc. to select the medical indicator resident within or on the image.

Figure 15:
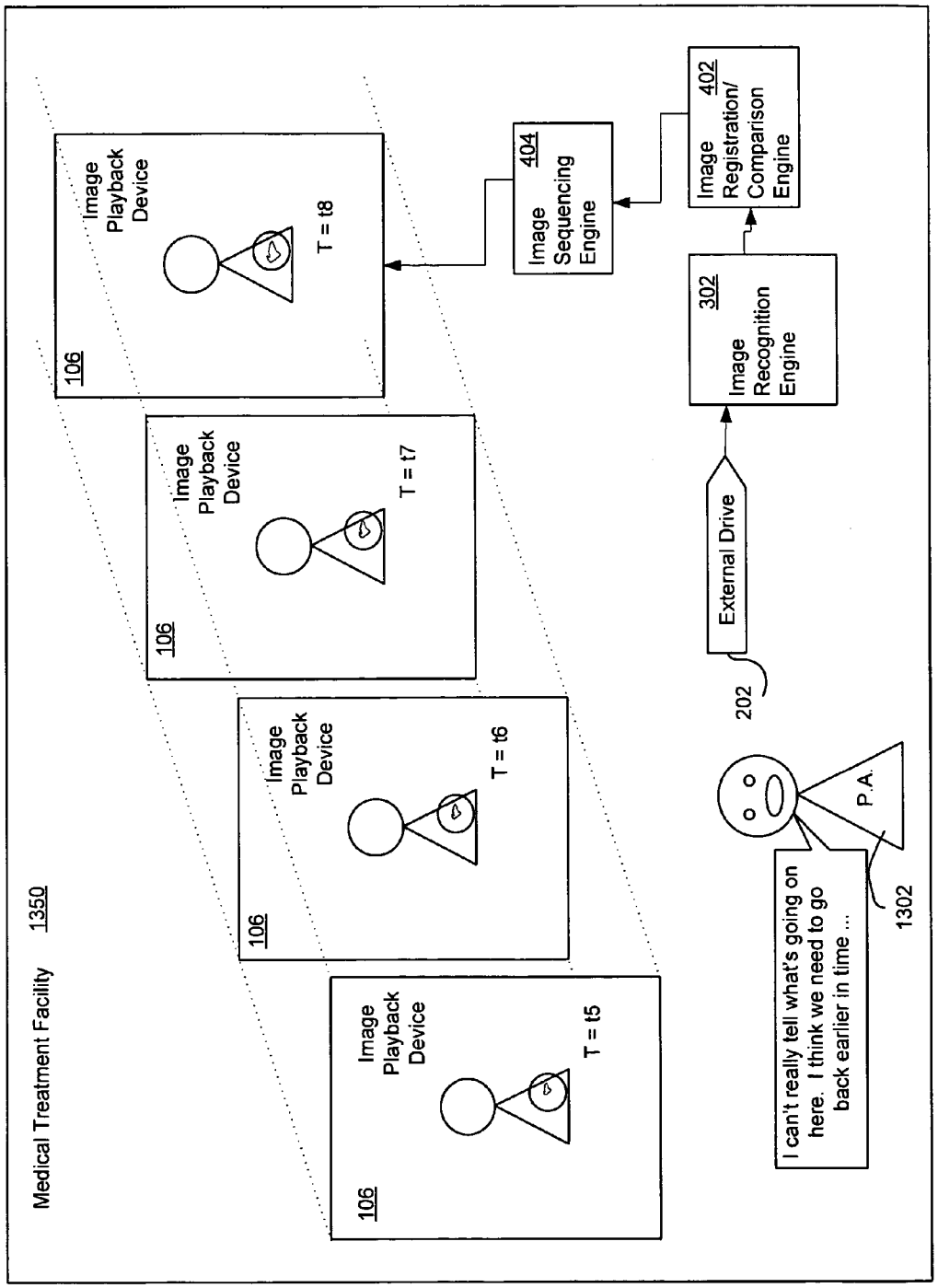
FIG. 15 illustrates a pictographic representation of the system presenting four (4) time sequenced views showing the growth of a lesion within a skin region over time (e.g., the previous 3 months, which in the current example is the extent of historical images on external drive 202).

With reference now to FIG. 15, illustrated is a pictographic representation of the system presenting four (4) time sequenced views showing the growth of a lesion within a skin region over time (e.g., the previous 3 months, which in the current example is the extent of historical images on external drive 202). Since there are four images shown for three months in the example, those skilled in the art will appreciate that image sequencing engine 404 is presenting in time-lapsed format. Shown is that the lesion is dark with an irregular border and growing, such as, for example, a melanoma region. Further depicted is physician's assistant 1302 commenting that she would prefer to see images from an earlier point in time.

Figure 16:
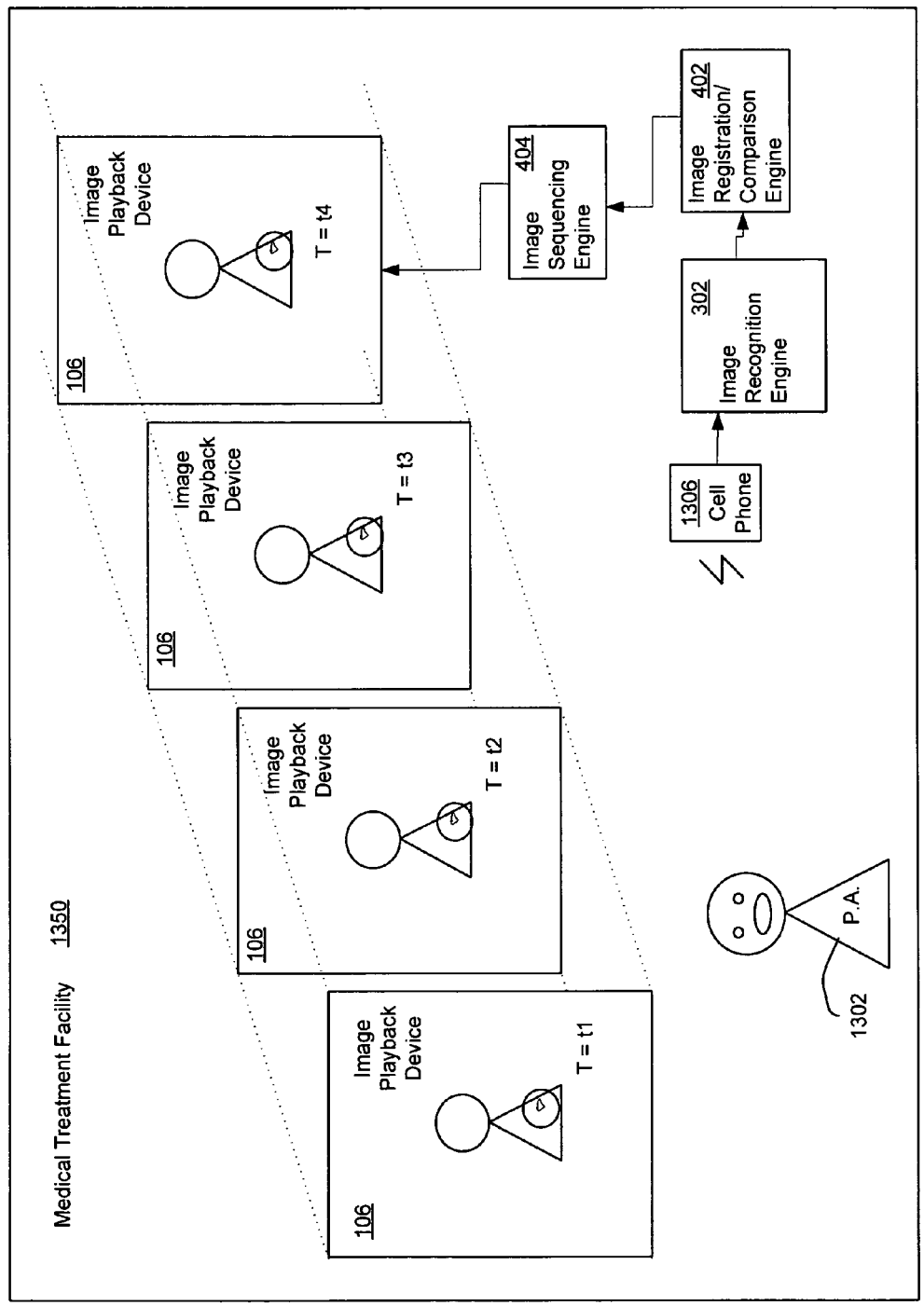
FIG. 16 shows a system substantially analogous to the system of FIG. 15, only modified such that image recognition system is now accessing older images of patient 1300 through cell phone 1306.

Referring now to FIG. 16, shown is a system substantially analogous to the system of FIG. 15, only modified such that image recognition system is now accessing older images of patient 1300 through cell phone 1300. Depicted is that the system is presenting older images of patient 1300 to physician's assistant 1302, and that those older images show a relatively long period where the lesion was relatively stable (e.g., not changing).

With reference now to FIG. 17, depicted is cell phone 1306 wirelessly accessing historical images of image storage device_3 206, such as over a cellular network. In one implementation, the historical images are presented to human and/or robotic expert systems. Those skilled in the art will appreciate that conventional wireless details (e.g., those having base stations and/or other underlying and/or supporting communications infrastructure) have been omitted from FIG. 17 for sake of clarity. In one implementation, both cell phone 1306 and the system resident in patient 1300's home 1600 have logic sufficient to allow access to the historical images of image storage device_3 206 in a manner such that the access is relatively transparent to image recognition engine 302; such logic is within the ambit of one skilled in the art in light of the logic herein and hence is not explicitly described for the sake of clarity. In addition, although FIG. 17 shows accessing of an image store internal to home 1600, the inventors point out that in some implementations the image store can be resident at another network location, such as at a base station server of a wireless network communications system. One implementation where such server storage is likely is one in which cell phone 1306 is used as an image capture device.

Figure 18:
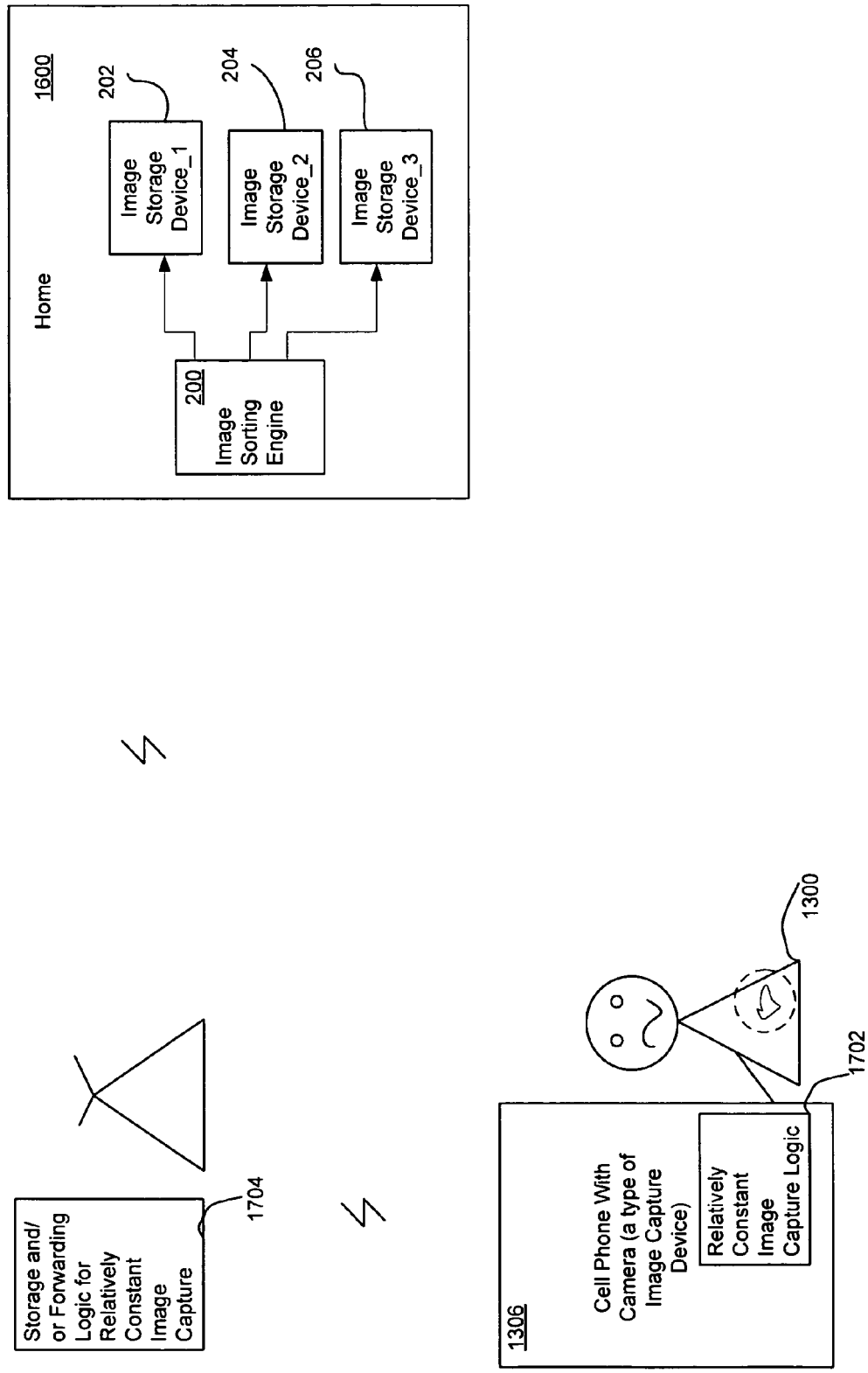
FIG. 18 illustrates an implementation in which a wireless device acts as an image capture device, which can prove particularly advantageous in regions with underutilized wireless network capacity (e.g., Asia, Europe, and/or North America).

Referring now to FIG. 18, illustrated is an implementation in which a wireless device acts as an image capture device, which can prove particularly advantageous in regions with underutilized wireless network capacity (e.g., Asia, Europe, and/or North America). Depicted is patient 1300 holding cell phone 1306. Cell phone 1306 is shown having a camera and relatively constant image capture logic 1702 which is logic that ensures that cell phone 1306 is relatively constantly capturing images. Illustrated is that relatively constant image capture logic 1702 causes transmission of the captured images to storage and/or forwarding logic for relatively constant image capture 1704, which is logic that stores images associated with either or both patient 1300 and/or user 1300's cell phone 1306. Depicted is that storage and/or forwarding logic for relatively constant image capture 1704 stores images received and/or transmits, and/or forwards, such images to image sorting engine 200 resident within patient 1300's home 1600. Image sorting image 200 in conjunction with image storage devices 202-206 function and/or interact in fashions analogous to those described elsewhere herein and hence are not expressly described here for sake of clarity. The inventors point out that while the various logic and/or storage and/or sorting and/or forwarding entities are depicted in FIG. 18 in similar locations as described elsewhere herein for sake of clarity, such entities can appear substantially anywhere within the system so long as the functionality described herein is achieved.

While some figures, such as FIGS. 15-18, have shown/described the historical images presented to physician's assistant 1302 (a medical expert) for sake of clarity, the inventors point out that in other implementations the historical images are presented to a robotic medical-expert system. The robotic medical-expert system can be automated systems (e.g., pattern recognition and/or other artificially intelligent systems) chosen from those available commercially and/or available from research institutions and/or within the ambit of those skilled in the art.

Figure 19:
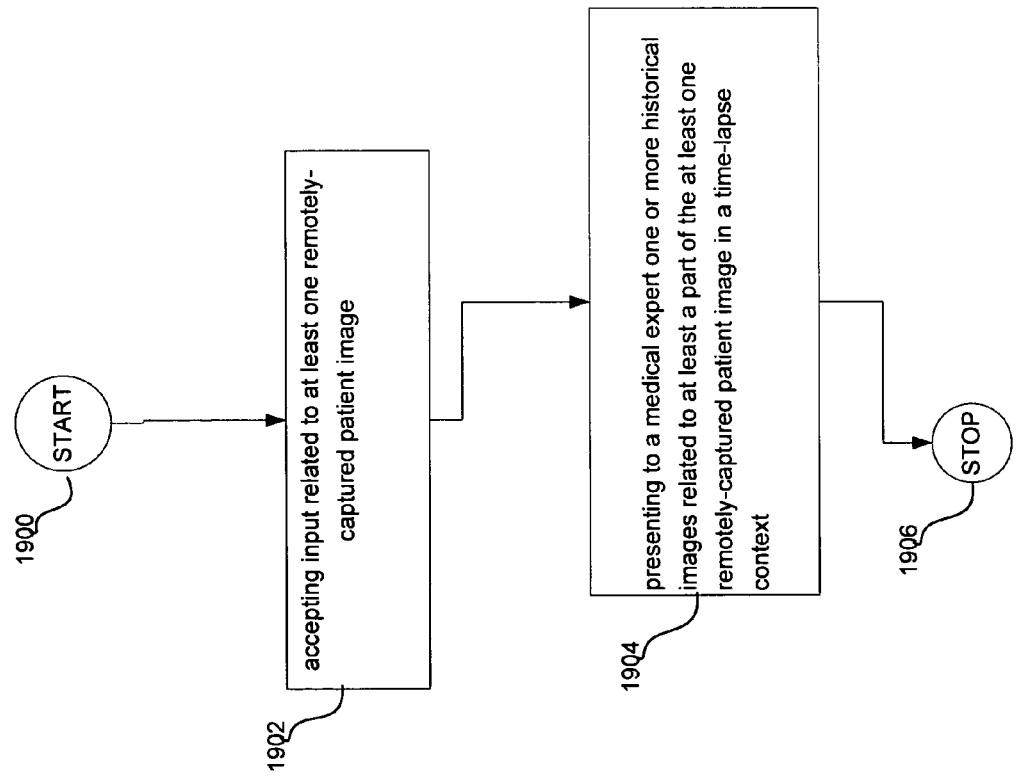
FIG. 19 shows a high-level logic flowchart of a process. Method step 1900 shows the start of the process.

With reference now to FIG. 19, shown is a high-level logic flowchart of a process. Method step 1900 shows the start of the process. Method step 1902 shows accepting input related to at least one remotely-captured patient image (e.g., image recognition system 302 retrieving and/or receiving input of one or more historical images from external drive 202 (FIG. 15) and/or cell phone 1306 (FIG. 16) and/or supporting components). Method step 1904 depicts presenting to a medical expert one or more historical images related to at least a part of the at least one remotely-captured patient image in a time-lapse context (e.g., such as shown/described in relation to presenting to human and/or robotic experts or expert systems such as shown/described in relation to FIGS. 15-18). Method step 1906 shows the end of the process. Those skilled in the art will appreciate that, in some implementations, the "at least a part of the image" can include but is not limited to a recognized region of an image or a recognized anchor point associated with an image which will provide the ability to do presentation on regions that both are and are not readily visually coordinated with an original field of view. For example, in a handheld mirror and/or cell phone implementations, a user might zoom in on a region of an image and then ask to see a time-lapse sequence of images representative of changes in that zoomed-in region, such that the zoomed-in region is not readily visually coordinated with the original unzoomed field of view of the mirror. The inventors point out that those skilled in the art will appreciate that while the zoomed-in region might not be easily visually coordinated with the unzoomed field of view, in some implementations the use of anchor points will allow coordination between the zoomed and unzoomed views. In addition, the inventors further point out that while examples set forth herein focus on anatomy and/or anatomical change for sake of clarity, the systems described herein can actually track and/or show a time lapse of substantially any object that may be reflected in the mirror and/or captured with the cell phone.

Figure 20:
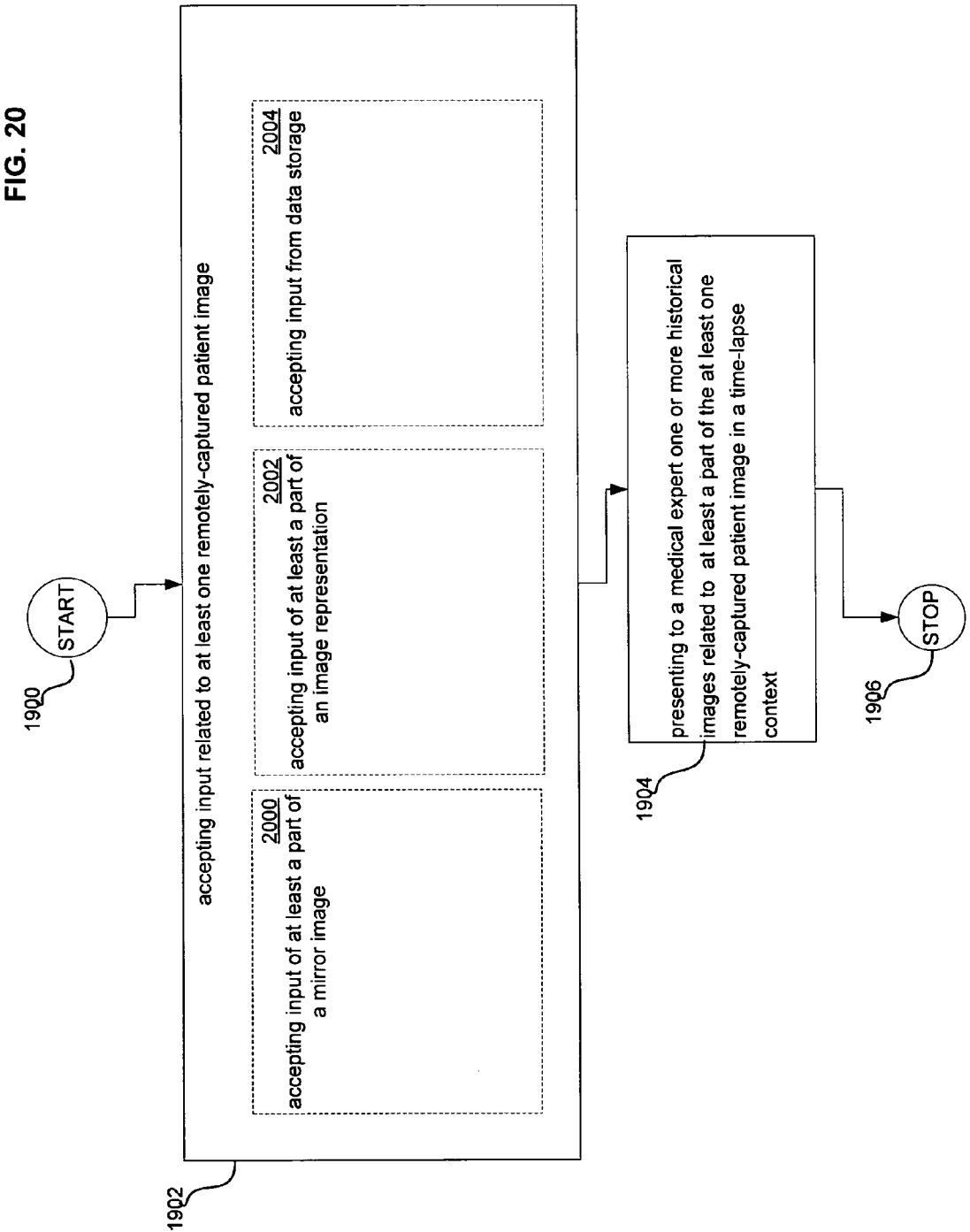
FIG. 20 shows a high-level logic flowchart depicting alternate implementations of the high-level logical flowchart of FIG. 19.

With reference now to FIG. 20, shown is a high-level logic flowchart depicting alternate implementations of the high-level logic flowchart of FIG. 19. Depicted is that in various alternate implementations, method step 1902 includes method step 2000, and/or method step 2002, and/or method step 2004. Method step 2000 shows accepting input of at least a part of a mirror image (e.g., image recognition system 302 retrieving and/or receiving input of one or more historical images captured by use of a mirror such as described elsewhere herein from external drive 202 (FIG. 15) and/or cell phone 1306 (FIG. 16) and/or supporting components). Method step 2002 depicts accepting input of at least a part of an image representation (e.g., image recognition system 302 retrieving and/or receiving input of one or more historical image representations (e.g., line drawings, infrared outlines, ultraviolet data, etc.) captured by use of a mirror such as described elsewhere herein from external drive 202 (FIG. 15) and/or cell phone 1306 (FIG. 16) and/or supporting components). The inventors point out that, as used here, the term "image" can generally also encompass an image representation, unless context dictates otherwise. Method step 2004 illustrates accepting input from data storage (e.g., from external drive 202, through cell phone 1306 accessing image storage device_3 206, etc.), where such data storage contains image data captured by use of a mirror such as described elsewhere herein and/or through a camera of cell phone 1306 (FIG. 18) and/or supporting components).

Figure 21:
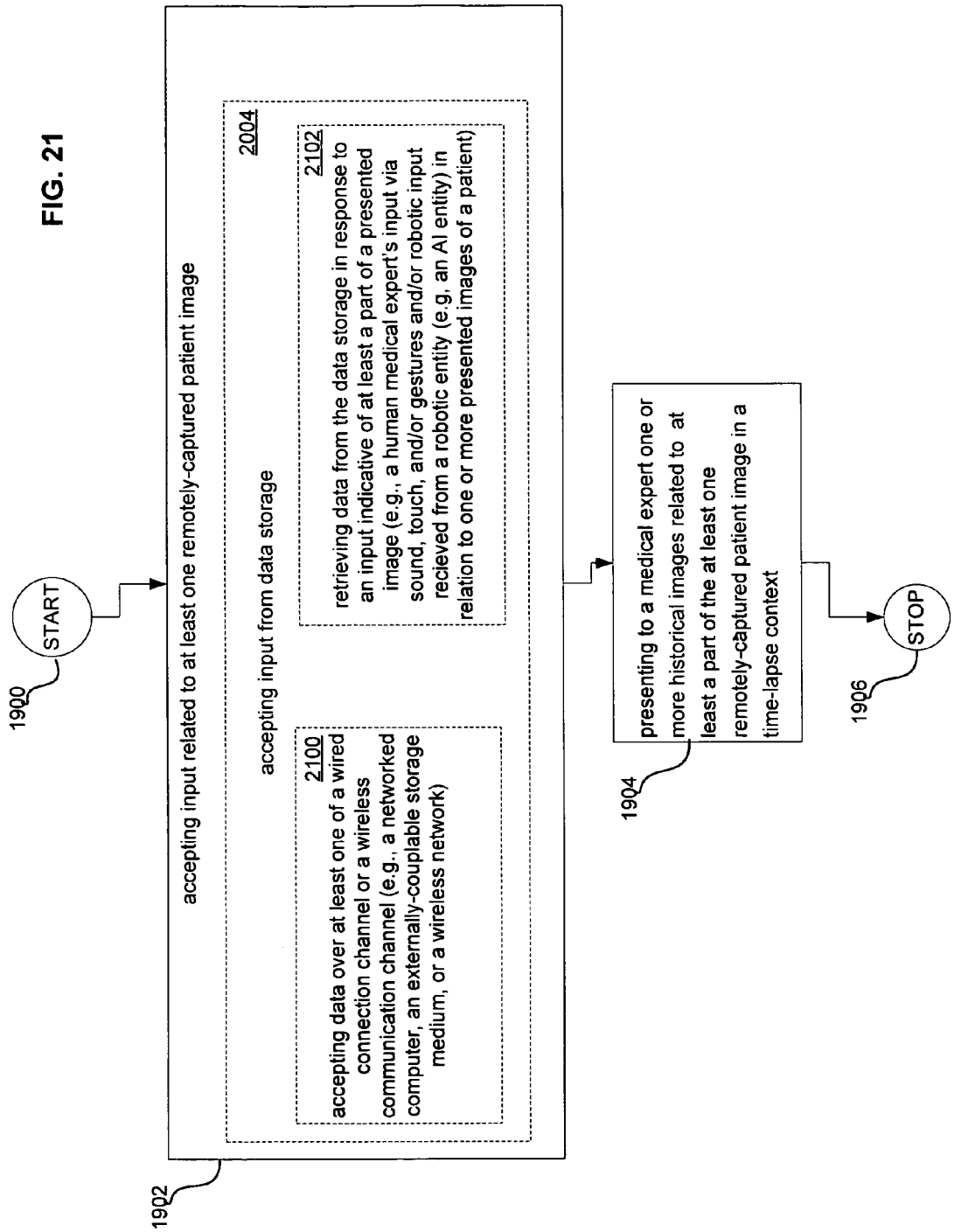
FIG. 21 shows a high-level logic flowchart depicting alternate implementations of the high-level logic flowchart of FIG. 20.

With reference now to FIG. 21, shown is a high-level logic flowchart depicting alternate implementations of the high-level logic flowchart of FIG. 20. Depicted is that in various alternate implementations, method step 2004 includes method step 2100 and/or method step 2102. Method step 2100 shows accepting data over at least one of a wired connection channel or a wireless communication channel (e.g., image recognition system 302 retrieving and/or receiving input of one or more historical images from at least one of a networked computer, an externally-couplable storage medium, or a wireless network). Method step 2102 depicts retrieving data from the data storage in response to an input indicative of at least a part of a presented image (e.g., retrieving in response to (a) physician's assistant 1302 input via sound, touch, and/or gestures and/or (b) robotic input received from a robotic entity, such as an AI entity in relation to one or more presented images of a patient (e.g., image recognition system 302 retrieving and/or receiving input of one or more historical image representations (e.g., line drawings, infrared outlines, ultraviolet data, etc.) captured by use of a mirror 100 and/or cell phone 1306 (FIG. 16) and/or supporting components such as described elsewhere herein from external drive 202 (FIG. 15) or through an external store accessed via cell phone 1306 (FIG. 17).

Figure 22:
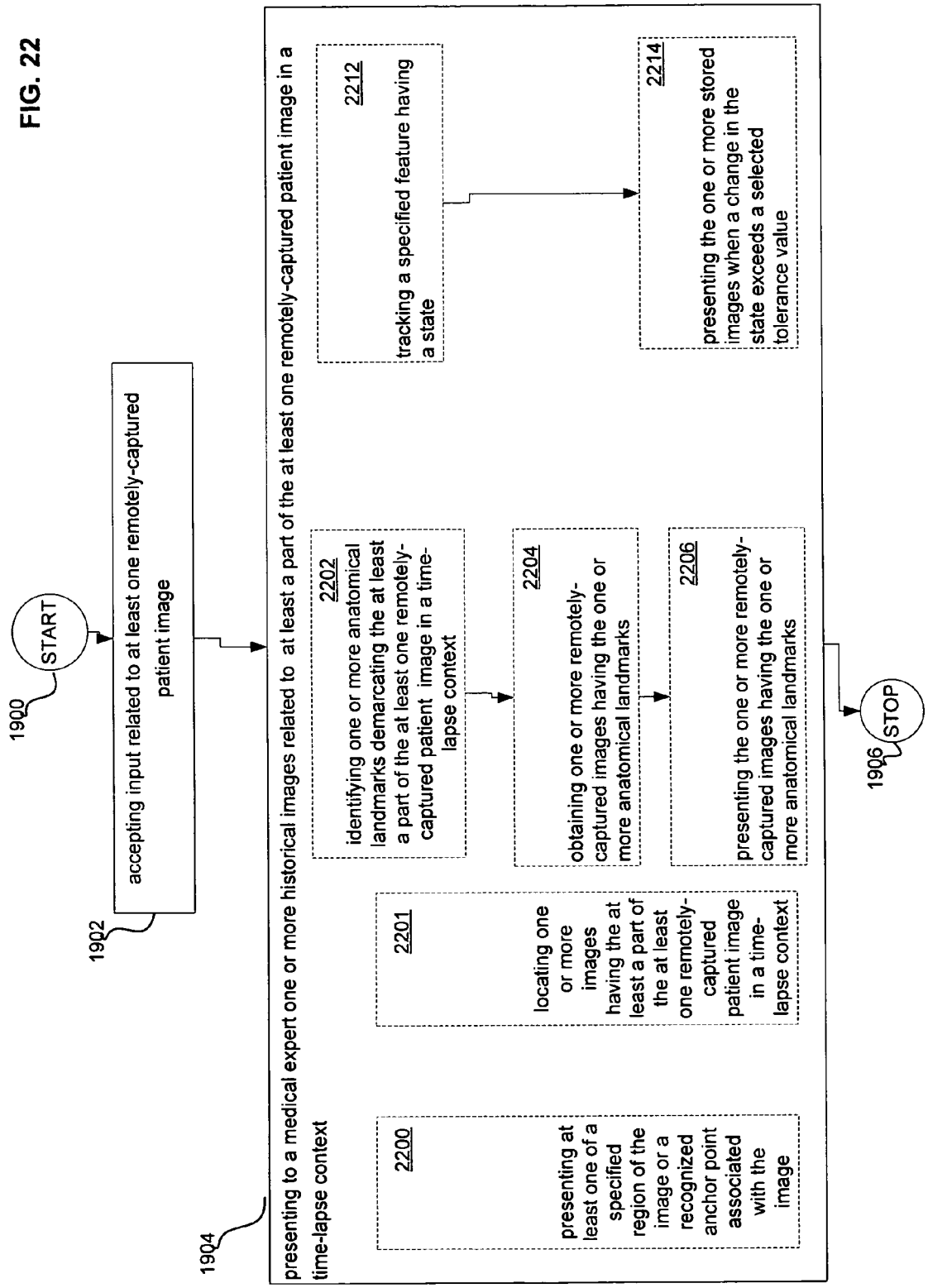
FIG. 22 depicts a high-level logic flowchart illustrating alternate implementations of the high-level logic flowchart of FIG. 10.

With reference now to FIG. 22, depicted is a high-level logic flowchart illustrating alternate implementations of the high-level logic flowchart of FIG. 10. Depicted is that in various alternate implementations, method step 1904 includes method step 2200, and/or method steps 2202-2206, and/or method steps 2212-2214. Method step 2200 shows one alternate implementation of presenting at least one of a specified region of the image or a recognized anchor point associated with the image (e.g., presenting all or part of a historical image having a feature identified by physician's assistant 1302 and/or a medical expert system, where the feature is characterized by a specified region of the image and/or a recognized anchor point). Method step 2201 shows one alternate implementation of locating one or more images having the at least a part of the at least one remotely-captured patient image in a time-lapse context. For example, locating the one or more images via image sorting engine 200, captured input storage device 300, image recognition engine 302, one or more of image storage devices 202-206, and/or cell phone 1306 communicating with a remote storage.

Continuing to refer to FIG. 22, method steps 2202-2206 depict another alternate embodiment. Method step 2202 illustrates identifying one or more anatomical landmarks demarcating the at least a part of the at least one remotely-captured patient image in a time-lapse context (e.g., via image sorting engine 200 and/or image recognition engine 302 processing on at least one retrieved historical image). Method step 2204 shows obtaining one or more remotely-captured images having the one or more anatomical landmarks (e.g., via image recognition engine 302 and/or image registration/comparison engine 402). Method step 2206 depicts presenting the one or more remotely-captured images having the one or more anatomical landmarks (e.g., via image playback device 106 and/or image sequencing engine 404). The inventors point out that while some examples herein show/describe obtaining remotely captured images that have the landmarks on or about the same physical structures, in other implementations the obtained remotely captured images have the landmarks on different physical structures. For instance, obtaining a set of images having landmark A on a second structure which in response to an identification of the same landmark A on a first structure (e.g. a physician is looking at an image of one eye of the patient and asks the system to present a history of the patient's other eye; a physician is looking at an image of one retina and asks to see a history of the patient's other retina; etc.). The inventors further point out that while some examples herein show/describe obtaining remotely captured images that have the landmarks on or about the same/different physical structures, in other implementations the obtained remotely captured images have the landmarks in the sense of medical context. For instance, while a finger and a toe might superficially be viewed as different landmarks, as used herein they may be viewed as practically similar landmarks in that both constitute instances of medical-context "extremities." Likewise, while a retina and a foot might superficially be viewed as different landmarks, as used herein they may be viewed as practically similar landmarks in that both constitute instances of indicators of medical-context diabetic complication severity (e.g., both the condition of the retina and the foot may be indicative of problems related to diabetes). Hence, as used herein, "one or more remotely-captured images having the one or more anatomical landmarks" is indicative of "having" in a broad, inclusive sense.

Continuing to refer to FIG. 22, method steps 2212-2214 illustrate yet another alternate embodiment. Method step 2212 shows tracking a specified feature having a state (e.g., via image registration/comparison engine 402 and/or its supporting components). Method step 2214 depicts presenting the one or more stored images when a change in the state exceeds a selected tolerance value (e.g., via image registration/comparison engine 402 and/or image sequencing engine 404 and/or their supporting components).

Figure 23:
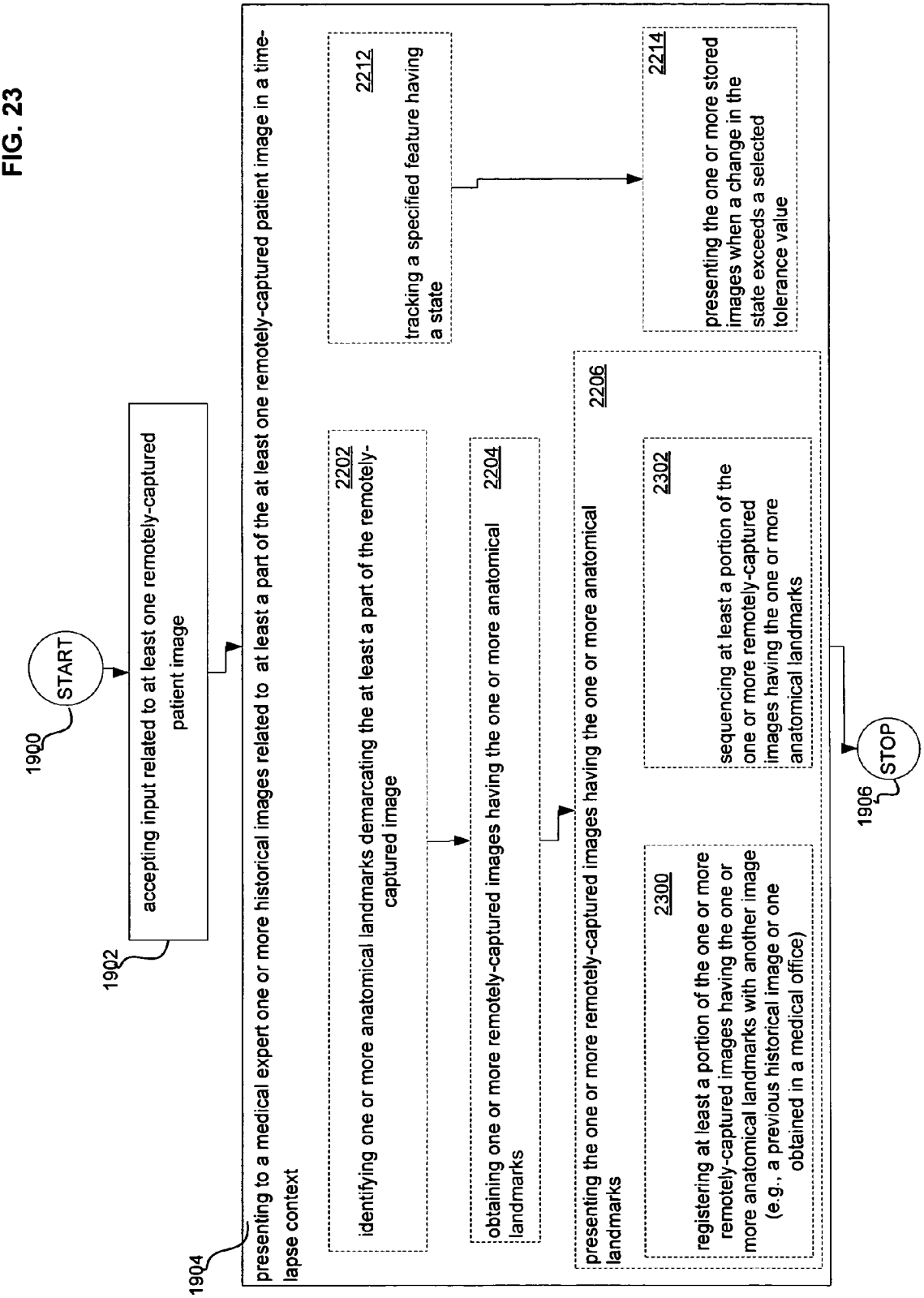
FIG. 23 shows a high-level logic flowchart depicting alternate implementations of the high-level logic flowchart of FIG. 22.

Referring now to FIG. 23, shown is a high-level logic flowchart depicting alternate implementations of the high-level logic flowchart of FIG. 22. Depicted is that in various alternate implementations, method step 2206 includes method step 2300 and/or method step 2302. Method step 2300 illustrates registering at least a portion of the one or more remotely-captured images having the one or more anatomical landmarks with another image (e.g., via image registration/comparison engine 402). Method step 2302 shows sequencing at least a portion of the one or more remotely-captured images having the one or more anatomical landmarks (e.g., via image sequencing engine 404).

Figure 24:
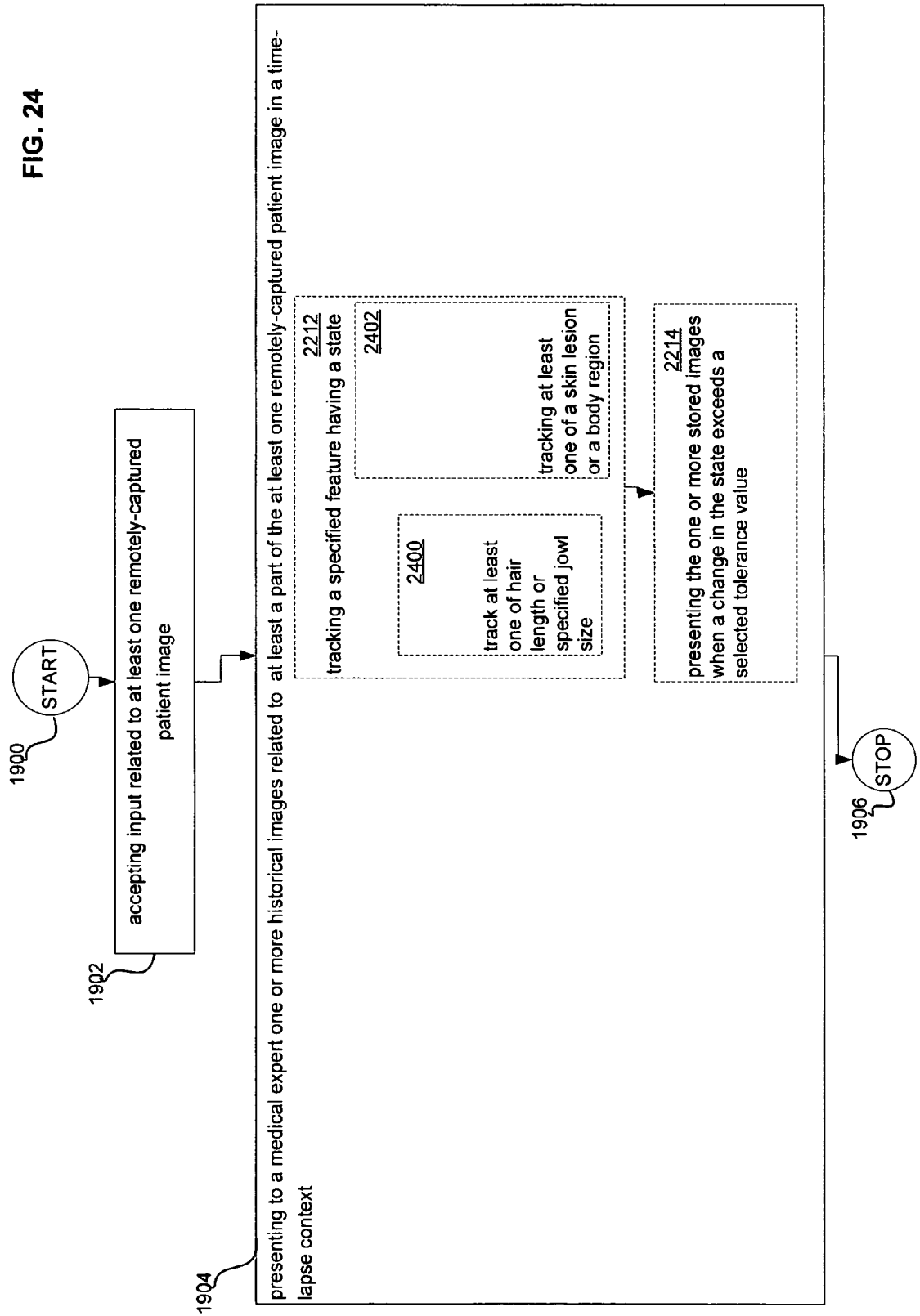
FIG. 24 depicts a high-level logic flowchart depicting alternate implementations of the high-level logic flowchart of FIG. 22.

With reference now to FIG. 24, depicted is a high-level logic flowchart depicting alternate implementations of the high-level logic flowchart of FIG. 22. Illustrated is that in various alternate implementations, method step 2212 includes method step 2400 and/or method step 2402. Method step 2400 illustrates tracking at least one of hair length, such as, for example, hair as on a suspicious mole, or jowl size, such as, for example, when a patient is suffering from the disease of aging (e.g., via image registration/comparison engine 402 and/or its supporting components). Method step 2402 shows tracking at least one of a skin lesion or a body region (e.g., via image recognition engine 302 and/or image registration/comparison engine 402 and/or their supporting components), which the inventors point out is helpful in a handheld mirror implementation.

Figure 25:
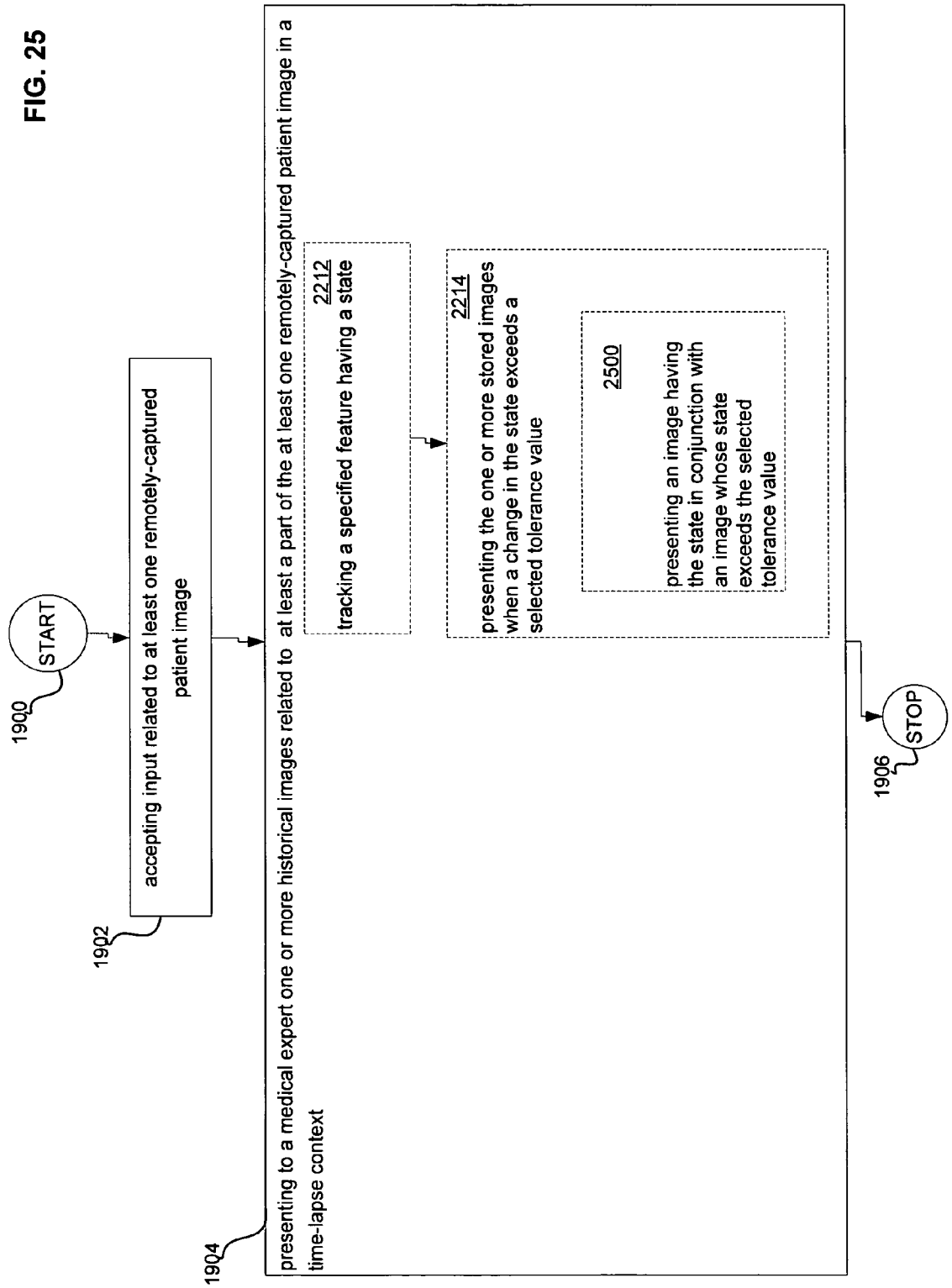
FIG. 25 illustrates a high-level logic flowchart depicting alternate implementations of the high-level logic flowchart of FIG. 24.

Referring now to FIG. 25, illustrated is a high-level logic flowchart depicting an alternate implementation of the high-level logic flowchart of FIG. 24. Shown is that in one alternate implementation, method step 2214 includes method step 2500. Method step 2500 shows presenting an image having the state in conjunction with an image whose state exceeds the selected tolerance value (e.g., via image recognition engine 302 and/or image registration/comparison engine 402 and/or image sequencing engine 404 and/or their supporting components).

Those skilled in the art will appreciate that the foregoing specific exemplary processes and/or devices and/or technologies are representative of more general processes and/or devices and/or technologies taught elsewhere herein, such as in the claims filed herewith and/or elsewhere in the present application.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will require optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in standard integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter subject matter described herein are capable of being distributed as a program product in a variety of forms, and that an illustrative embodiment of the subject matter subject matter described herein applies equally regardless of the particular type of signal bearing media used to actually carry out the distribution. Examples of a signal bearing media include, but are not limited to, the following: recordable type media such as floppy disks, hard disk drives, CD ROMs, digital tape, and computer memory; and transmission type media such as digital and analog communication links using TDM or IP based communication links (e.g., packet links).

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and electrical circuitry forming a communications device (e.g., a modem, communications switch, or optical-electrical equipment).

Those skilled in the art will recognize that it is common within the art to describe devices and/or processes in the fashion set forth herein, and thereafter use standard engineering practices to integrate such described devices and/or processes into image processing systems. That is, at least a portion of the devices and/or processes described herein can be integrated into an image processing system via a reasonable amount of experimentation. Those having skill in the art will recognize that a typical image processing system generally includes one or more of a system unit housing, a video display device, a memory such as volatile and non-volatile memory, processors such as microprocessors and digital signal processors, computational entities such as operating systems, drivers, and applications programs, one or more interaction devices, such as a touch pad or screen, control systems including feedback loops and control motors (e.g., feedback for sensing lens position and/or velocity; control motors for moving/distorting lenses to give desired focuses. A typical image processing system may be implemented utilizing any suitable commercially available components, such as those typically found in digital still systems and/or digital motion systems.

All of the above U.S. patents, U.S. patent application publications, U.S. patent applications, foreign patents, foreign patent applications, and non-patent publications referred to in this specification and/or listed in any Application Data Sheet are incorporated herein by reference, in their entireties.

The herein described aspects depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from this subject matter described herein and its broader aspects and, therefore, the appended claims are to encompass within their scope all such changes and modifications as are within the true spirit and scope of this subject matter described herein. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.).

In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.).

The invention claimed is:

1. A method comprising:
   accepting input related to at least one remotely-captured patient image wherein said accepting input related to at least one remotely-captured patient image is performed via at least one of a machine, article of manufacture, or composition of matter; and
   presenting to a medical expert one or more historical images related to at least a part of the at least one remotely-captured patient image in a time-lapse context, wherein said presenting to a medical expert one or more historical images related to at least a part of the at least one remotely-captured patient image in a time-lapse context is performed via at least one of a machine, article of manufacture, or composition of matter and wherein said presenting to a medical expert one or more historical images related to at least a part of the at least one remotely-captured patient image in a time-lapse context further comprises:
      identifying one or more anatomical landmarks demarcating the at least a part of the at least one remotely-captured patient image in a time-lapse context;
      obtaining one or more remotely-captured images having the one or more anatomical landmarks; and
      presenting the one or more remotely-captured images having the one or more anatomical landmarks.

2. The method of claim 1, wherein said accepting input related to at least one remotely-captured patient image further comprises:
   accepting input of at least a part of a mirror image.

3. The method of claim 1, wherein said accepting input related to at least one remotely-captured patient image further comprises:
   accepting input of at least a part of an image representation.

4. The method of claim 1, wherein said accepting input related to at least one remotely-captured patient image further comprises:
   accepting input from data storage.

5. The method of claim 4, wherein said accepting input from data storage further comprises:
   accepting data over at least one of a wired connection channel or a wireless communication channel.

6. The method of claim 4, wherein said accepting input from data storage further comprises:
   retrieving data from the data storage in response to an input indicative of at least a part of a presented image.

7. The method of claim 1, wherein said presenting to a medical expert one or more historical images related to at least a part of the at least one remotely-captured patient image in a time-lapse context further comprises:
   presenting at least one of a specified region of the image or a recognized anchor point associated with the image.

8. The method of claim 1, wherein said presenting to a medical expert one or more historical images related to at least a part of the at least one remotely-captured patient image in a time-lapse context further comprises:
   locating one or more images having the at least a part of the at least one remotely-captured patient image in a time-lapse context.

9. The method of claim 1, wherein said presenting the one or more remotely-captured images having the one or more anatomical landmarks further comprises:
   registering at least a portion of the one or more remotely-captured images having the one or more anatomical landmarks with another image.

10. The method of claim 1, wherein said presenting the one or more remotely-captured images having the one or more anatomical landmarks further comprises:
    sequencing at least a portion of the one or more remotely-captured images having the one or more anatomical landmarks.

11. The method of claim 1, wherein said presenting to a medical expert one or more historical images related to at least a part of the at least one remotely-captured patient image in a time-lapse context further comprises:
    tracking a specified feature having a state; and
    presenting the one or more stored images when a change in the state exceeds a selected tolerance value.

12. The method of claim 11, wherein said tracking a specified feature having a state further comprises:
    tracking at least one of hair length or jowl size.

13. The method of claim 11, wherein said tracking a specified feature having a state further comprises:
    tracking at least one of a skin lesion or a body region.

14. The method of claim 11, wherein said presenting the one or more stored images when a change in the state exceeds a selected tolerance value further comprises:
    presenting an image having the state in conjunction with an image whose state exceeds the selected tolerance value.

15. A system comprising:
    means for accepting input related to at least one remotely-captured patient image; and
    means for presenting to a medical expert one or more historical images related to at least a part of the at least one remotely-captured patient image in a time-lapse context, wherein said means for presenting to a medical expert one or more historical images related to at least a part of the at least one remotely-captured patient image in a time-lapse context further comprises:
       means for identifying one or more anatomical landmarks demarcating the at least a part of the at least one remotely-captured patient image in a time-lapse context;
       means for obtaining one or more remotely-captured images having the one or more anatomical landmarks; and
       means for presenting the one or more remotely-captured images having the one or more anatomical landmarks.

16. The system of claim 15, wherein said means for accepting input related to at least one remotely-captured patient image further comprises:
    means for accepting input of at least a part of a mirror image.

17. The system of claim 15, wherein said means for accepting input related to at least one remotely-captured patient image further comprises:
    means for accepting input of at least a part of an image representation.

18. The system of claim 15, wherein said means for accepting input related to at least one remotely-captured patient image further comprises:
    means for accepting input from data storage.

19. The system of claim 18, wherein said means for accepting input from data storage further comprises:

means for accepting data over at least one of a wired connection channel or a wireless communication channel.

20. The system of claim 18, wherein said means for accepting input from data storage further comprises:
means for retrieving data from the data storage in response to an input indicative of at least a part of a presented image.

21. The system of claim 15, wherein said means for presenting to a medical expert one or more historical images related to at least a part of the at least one remotely-captured patient image in a time-lapse context further comprises:
means for presenting at least one of a specified region of the image or a recognized anchor point associated with the image.

22. The system of claim 15, wherein said means for presenting to a medical expert one or more historical images related to at least a part of the at least one remotely-captured patient image in a time-lapse context further comprises:
means for locating one or more images having the at least a part of the at least one remotely-captured patient image in a time-lapse context.

23. The system of claim 15, wherein said means for presenting the one or more remotely-captured images having the one or more anatomical landmarks further comprises:
means for registering at least a portion of the one or more remotely-captured images having the one or more anatomical landmarks with another image.

24. The system of claim 15, wherein said means for presenting the one or more remotely-captured images having the one or more anatomical landmarks further comprises:
means for sequencing at least a portion of the one or more remotely-captured images having the one or more anatomical landmarks.

25. The system of claim 15, wherein said means for presenting to a medical expert one or more historical images related to at least a part of the at least one remotely-captured patient image in a time-lapse context further comprises:
means for tracking a specified feature having a state; and
means for presenting the one or more stored images when a change in the state exceeds a selected tolerance value.

26. The system of claim 25, wherein said means for tracking a specified feature having a state further comprises:
means for tracking at least one of hair length or jowl size.

27. The system of claim 25, wherein said means for tracking a specified feature having a state further comprises:
means for tracking at least one of a skin lesion or a body region.

28. The system of claim 25, wherein said means for presenting the one or more stored images when a change in the state exceeds a selected tolerance value further comprises:
means for presenting an image having the state in conjunction with an image whose state exceeds the selected tolerance value.

29. A computer program product comprising:
an article of manufacture including a signal-bearing medium bearing:
one or more instructions for accepting input related to at least one remotely-captured patient image; and
one or more instructions for presenting to a medical expert one or more historical images related to at least a part of the at least one remotely-captured patient image in a time-lapse context, wherein said one or more instructions for presenting to a medical expert one or more historical images related to at least a part of the at least one remotely-captured patient image in a time-lapse context further comprises:
one or more instructions for identifying one or more anatomical landmarks demarcating the at least a part of the at least one remotely-captured patient image in a time-lapse context;
one or more instructions for obtaining one or more remotely-captured images having the one or more anatomical landmarks; and
one or more instructions for presenting the one or more remotely-captured images having the one or more anatomical landmarks.

30. The computer program product of claim 29, wherein said article of manufacture including a signal-bearing medium comprises:
a computer-readable medium.

31. The computer program product of claim 29, wherein said article of manufacture including a signal-bearing medium comprises:
a recordable medium.

32. The computer program product of claim 29, wherein said article of manufacture including a signal-bearing medium comprises:
a transmission medium.

33. The computer program product of claim 29, wherein said one or more instructions for accepting input related to at least one remotely-captured patient image further comprises:
one or more instructions for accepting input of at least a part of a mirror image.

34. The computer program product of claim 29, wherein said one or more instructions for accepting input related to at least one remotely-captured patient image further comprises:
one or more instructions for accepting input of at least a part of an image representation.

35. The computer program product of claim 29, wherein said one or more instructions for accepting input related to at least one remotely-captured patient image further comprises:
one or more instructions for accepting input from data storage.

36. The computer program product of claim 35, wherein said one or more instructions for accepting input from data storage further comprises:
one or more instructions for accepting data over at least one of a wired connection channel or a wireless communication channel.

37. The computer program product of claim 35, wherein said one or more instructions for accepting input from data storage further comprises:
one or more instructions for retrieving data from the data storage in response to an input indicative of at least a part of a presented image.

38. The computer program product of claim 29, wherein said one more instructions for presenting to a medical expert one or more historical images related to at least a part of the at least one remotely-captured patient image in a time-lapse context further comprises:
one or more instructions for presenting at least one of a specified region of the image or a recognized anchor point associated with the image.

39. The computer program product of claim 29, wherein said one or more instructions for presenting to a medical expert one or more historical images related to at least a part of the at least one remotely-captured patient image in a time-lapse context further comprises:
one or more instructions for locating one or more images having the at least a part of the at least one remotely-captured patient image in a time-lapse context.

40. The computer program product of claim 29, wherein said one more instructions for presenting the one or more remotely-captured images having the one or more anatomical landmarks further comprises:

one or more instructions for registering at least a portion of the one or more remotely-captured images having the one or more anatomical landmarks with another image.

41. The computer program product of claim 29, wherein said one more instructions for presenting the one or more remotely-captured images having the one or more anatomical landmarks further comprises:

one or more instructions for sequencing at least a portion of the one or more remotely-captured images having the one or more anatomical landmarks.

42. The computer program product of claim 29, wherein said one more instructions for presenting to a medical expert one or more historical images related to at least a part of the at least one remotely-captured patient image in a time-lapse context further comprises:

means for tracking a specified feature having a state; and one or more instructions for presenting the one or more stored images when a change in the state exceeds a selected tolerance value.

43. The computer program product of claim 42, wherein said one more instructions for tracking a specified feature having a state further comprises:

one or more instructions for tracking at least one of hair length or jowl size.

44. The computer program product of claim 42, wherein said one more instructions for tracking a specified feature having a state further comprises:

one or more instructions for tracking at least one of a skin lesion or a body region.

45. The computer program product of claim 42, wherein said one more instructions for presenting the one or more stored images when a change in the state exceeds a selected tolerance value further comprises:

one or more instructions for presenting an image having the state in conjunction with an image whose state exceeds the selected tolerance value.

46. A system comprising:

circuitry for accepting input related to at least one remotely-captured patient image; and circuitry for presenting to a medical expert one or more historical images related to at least a part of the at least one remotely-captured patient image in a time-lapse context, wherein said circuitry for presenting to a medical expert one or more historical images related to at least a part of the at least one remotely-captured patient image in a time-lapse context further comprises:

circuitry for identifying one or more anatomical landmarks demarcating the at least a part of the at least one remotely-captured patient image in a time-lapse context;

circuitry for obtaining one or more remotely-captured images having the one or more anatomical landmarks; and circuitry for presenting the one or more remotely-captured images having the one or more anatomical landmarks.

\* \* \* \* \*

UNITED STATES PATENT AND TRADEMARK OFFICE
CERTIFICATE OF CORRECTION

PATENT NO. : 7,657,125 B2
APPLICATION NO. : 10/972319
DATED : February 2, 2010
INVENTOR(S) : Paul G. Allen et al.

Page 1 of 1

It is certified that error appears in the above-identified patent and that said Letters Patent is hereby corrected as shown below:

Column 20, line 53, the following text "said one more" should read --said one or more--

Column 21, line 2, the following text "said one more" should read --said one or more--

Column 21, line 9, the following text "said one more" should read --said one or more--

Column 21, line 16, the following text "said one more" should read --said one or more--

Column 21, line 25, the following text "said one more" should read --said one or more--

Column 21, line 30, the following text "said one more" should read --said one or more--

Column 22, line 4, the following text "said one more" should read --said one or more--

Signed and Sealed this

Fifteenth Day of June, 2010

David J. Kappos
*Director of the United States Patent and Trademark Office*

UNITED STATES PATENT AND TRADEMARK OFFICE
CERTIFICATE OF CORRECTION

PATENT NO. : 7,657,125 B2 Page 1 of 1
APPLICATION NO. : 10/972319
DATED : February 2, 2010
INVENTOR(S) : Paul G. Allen et al.

It is certified that error appears in the above-identified patent and that said Letters Patent is hereby corrected as shown below:

Title Page:

(*) Notice

Delete "by 794 days" and insert --by 1380 days--.

Signed and Sealed this

Thirty-first Day of August, 2010

David J. Kappos
*Director of the United States Patent and Trademark Office*